Figure 1:
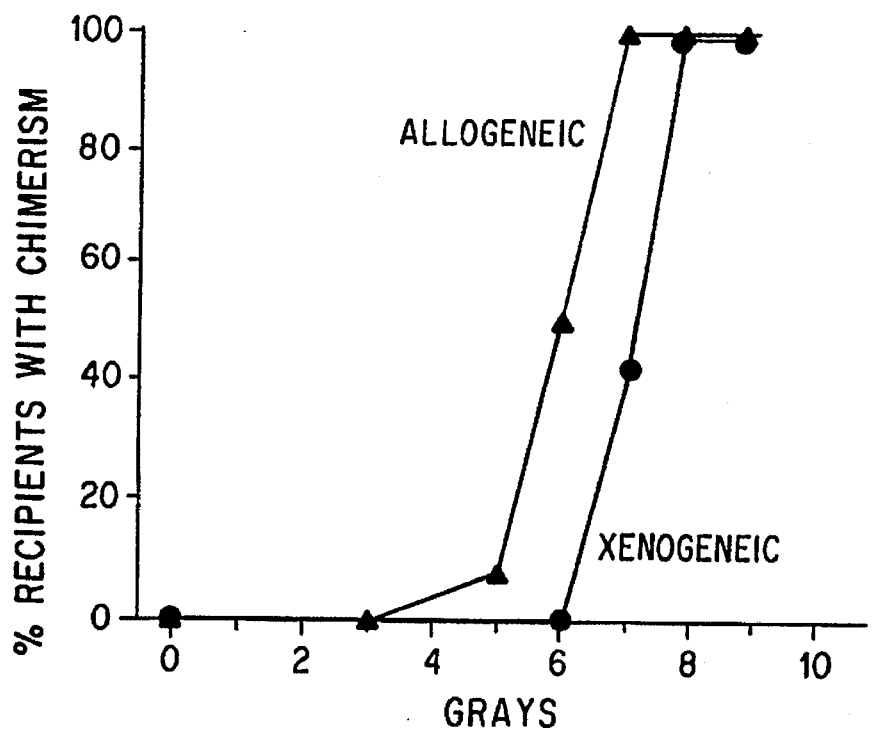

United States Patent [19]

Ildstad

[11] Patent Number: 5,635,156
[45] Date of Patent: Jun. 3, 1997

[54] NON-LETHAL METHODS FOR CONDITIONING A RECIPIENT FOR BONE MARROW TRANSPLANTATION

[75] Inventor: Suzanne T. Ildstad, Pittsburgh, Pa.

[73] Assignee: University of Pittsburgh, Pittsburgh, Pa.

[21] Appl. No.: 337,785

[22] Filed: Nov. 14, 1994

Related U.S. Application Data

[63] Continuation-in-part of Ser. No. 120,256, Sep. 13, 1993, Pat. No. 5,514,364.

[51] Int. Cl.⁶ .......................... A61K 43/00; A61K 31/00; A61K 5/00
[52] U.S. Cl. ................ 424/1.49; 424/130.1; 424/141.1; 424/152.1; 424/153.1; 424/154.1; 424/178.1; 424/181.1; 424/183.1; 600/1; 604/20
[58] Field of Search ................ 424/1.49, 1.53, 424/130.1, 141.1, 178.1, 183.1, 152.1, 153.1, 154.1, 181.1; 600/1, 9, 13, 14; 604/20

[56] References Cited

U.S. PATENT DOCUMENTS

| | | | |
|---|---|---|---|
| 4,500,637 | 2/1985 | Neville, Jr. et al. | 435/2 |
| 4,998,931 | 3/1991 | Slichter et al. | 604/20 |
| 5,178,858 | 1/1993 | Reichert et al. | 424/85.8 |
| 5,187,266 | 2/1993 | Farguhar et al. | 536/6.4 |
| 5,273,738 | 12/1993 | Matthews et al. | 424/1.1 |
| 5,374,658 | 12/1994 | Lau | 514/557 |
| 5,504,092 | 4/1996 | Nilsson et al. | 514/312 |
| 5,514,364 | 5/1996 | Ildstad | 424/1.49 |

OTHER PUBLICATIONS

Down et al., "Synogeneic and Allogeneic Bone Marrow Engraftment After Total Body Irradiation," *Blood*, 77(3), Jan. 1, 1991, pp. 661–669.

Pierce et al., "Effects of Thy-1⁺Cell Depletion . . . ", *Transplantation*, 48(2), Aug. 1989, pp. 289–296.

Gassmann et al., "Immune Reactivity After High-Dose Irradiation," *Transplantation*, 41(3), Mar. 1986, pp. 380–384.

Pierce et al., "The Role of Donor Lymphoid Cells . . . ", *Transplantation*, 40(6), Dec. 1985, pp. 702–707.

Nakamura et al., "Graft Rejection by Cytolytic T Cells . . . ," *Transplantation*, 49(2), Feb. 1990, pp. 453–458.

Antin et al., "Selective Depletion of Bone Marrow T Lymphocytes . . . ," *Blood*, 78(8), 1991, pp. 2139–2149, abstracted in Biosis 92:6551.

*Primary Examiner*—John Kight
*Assistant Examiner*—Lara E. Chapman
*Attorney, Agent, or Firm*—Pennie & Edmonds

[57] ABSTRACT

The present invention relates to non-lethal methods of conditioning a recipient for bone marrow transplantation. In particular, it relates to the use of nonlethal doses of total body irradiation, total lymphoid irradiation cell type-specific antibodies, especially antibodies directed to bone marrow stromal cell markers, cytotoxic drugs, or a combination thereof. The methods of the invention have a wide range of applications, including, but not limited to, the conditioning of an individual for hematopoietic reconstitution by bone marrow transplantation for the treatment of hematologic malignancies, hematologic disorders, autoimmunity, infectious diseases such as acquired immunodeficiency syndrome, and the engraftment of bone marrow cells to induce tolerance for solid organ, tissue and cellular transplantation.

10 Claims, 11 Drawing Sheets

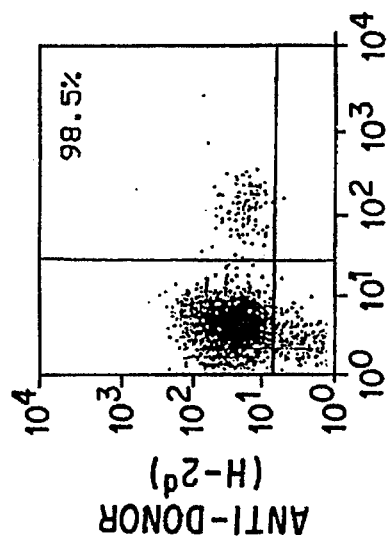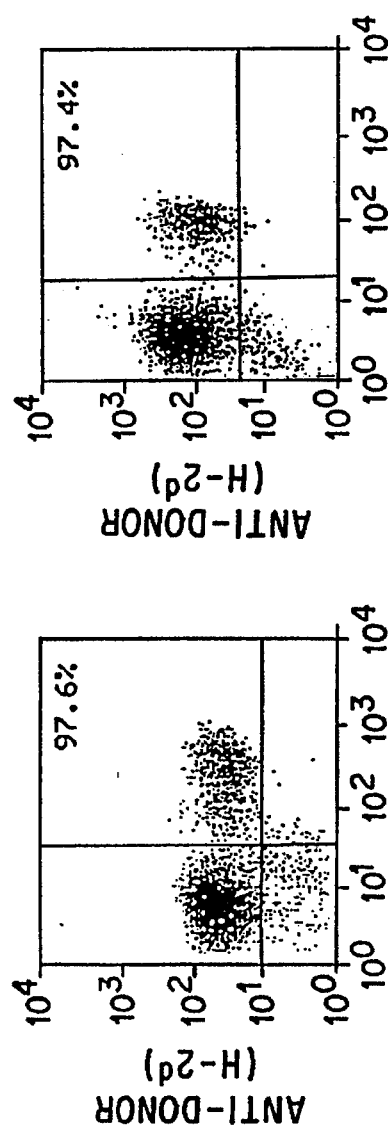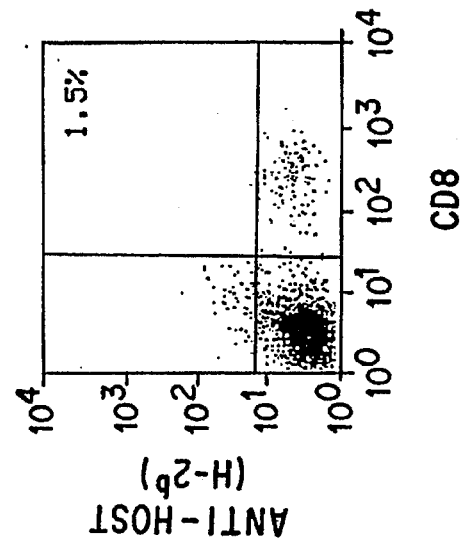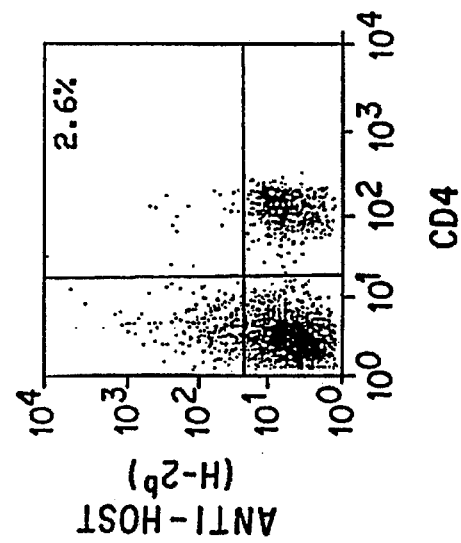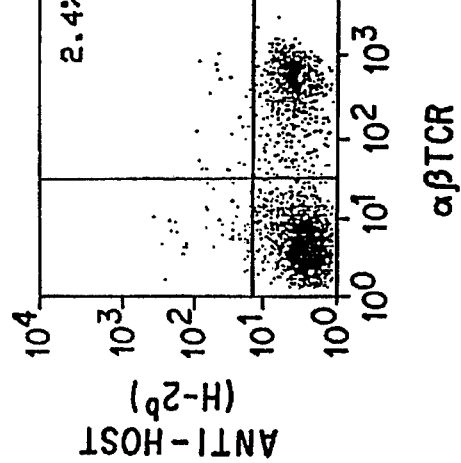

NON-LETHAL METHODS FOR CONDITIONING A RECIPIENT FOR BONE MARROW TRANSPLANTATION

The present application is a continuation-in-part of application Ser. No. 08/120,256 filed Sep. 13, 1993 now U.S. Pat. No. 5,514,364, which is incorporated by reference herein in its entirety.

TABLE OF CONTENTS
1. INTRODUCTION
2. BACKGROUND OF THE INVENTION
3. SUMMARY OF THE INVENTION
4. BRIEF DESCRIPTION OF THE DRAWINGS
5. DETAILED DESCRIPTION OF THE INVENTION
   5.1. NON-LETHAL CONDITIONING REGIMENS FOR DONOR CELL ENGRAFTMENT
   5.2. ANTIBODY FOR USE IN CONDITIONING
   5.3. USES OF ANTIBODIES TO STROMAL CELLS
6. EXAMPLE: ALLOGENEIC BONE MARROW CELLS ENGRAFT IN RECIPIENTS CONDITIONED BY NON-LETHAL METHODS
   6.1. MATERIALS AND METHODS
      6.1.1. ANIMALS
      6.1.2. FLOW CYTOMETRY
      6.1.3. PLATELET ISOLATION
      6.1.4. GLUCOSE PHOSPHATE ISOMERASE-1 (GPI-1) ASSAY
      6.1.5. SKIN GRAFTING
      6.1.6. MIXED LYMPHOCYTE REACTIONS (MLR)
      6.1.7. CELL-MEDIATED LYMPHOLYSIS (CML)
   6.2. RESULTS
      6.2.1. ALLOGENEIC ENGRAFTMENT WITH NON-LETHAL TOTAL BODY IRRADIATION ALONE: DOSE-TITRATION OF RADIATION-BASED CONDITIONING
      6.2.2. ENGRAFTMENT OF ALLOGENEIC BONE MARROW IS ENHANCED BY ANTI-LYMPHOCYTE GLOBULIN
      6.2.3. INFLUENCE OF CELL DOSE IN THEALLOGENEIC INOCULUM ON ENGRAFTMENT WITH ALG AND TBI CONDITIONING
      6.2.4. ALLOGENEIC ENGRAFTMENT IS ENHANCED BY THE ADDITION OF CYCLOPHOSPHAMIDE TO THE ESTABLISHED RADIATION-BASED CONDITIONING
      6.2.5. INFLUENCE OF TIMING OF TBI ON ALLOENGRAFTMENT IN RECIPIENTS CONDITIONED WITH ANTI-LYMPHOCYTE GLOBULIN OR CYCLOPHOSPHAMIDE
      6.2.6. CHARACTERIZATION OF A NONLETHAL RADIATION-BASED APPROACH FOR CYTOREDUCTION
      6.2.7. NONLETHAL MIXED CHIMERAS: EVIDENCE FOR MULTILINEAGE MIXED CHIMERISM
      6.2.8. EVIDENCE THAT ERYTHROCYTES AND PLATELETS IN ALLOGENEIC CHIMERAS ARE OF BOTH SYNGENEIC AND ALLOGENEIC ORIGIN
      6.2.9. EVIDENCE FOR SPECIFIC TOLERANCE IN VIVO TO DONOR-TYPE SKIN GRAFTS
      6.2.10. FUNCTIONAL DONOR-SPECIFIC TOLERANCE IN VITRO
      6.2.11. NONLETHAL PREPARATIVE REGIMENS RESULT IN STABLE ALLOGENEIC CHIMERISM AND EXCELLENT LONG-TERM RECIPIENT SURVIVAL AND NO EVIDENCE FOR GVHD
      6.2.12. ALLOGENEIC ENGRAFTMENT AFTER CONDITIONING WITH NONLETHAL TOTAL BODY IRRADIATION, ANTI-LYMPHOCYTE GLOBULIN AND CYCLOPHOSPHAMIDE
7. EXAMPLE: XENOGENEIC BONE MARROW CELLS ENGRAFT IN RECIPIENTS CONDITIONED BY NON-LETHAL METHODS
   7.1. RESULTS

1. INTRODUCTION

The present invention relates to non-lethal methods of conditioning a recipient for bone marrow transplantation. In particular, it relates to the use of nonlethal doses of total body irradiation, total lymphoid irradiation, cell type-specific antibodies, especially antibodies directed to bone marrow stromal cell markers, cytotoxic drugs, or a combination thereof. The methods of the invention have a wide range of applications, including, but not limited to, the conditioning of an individual for hematopoietic reconstitution by bone marrow transplantation for the treatment of hematologic malignancies, hematologic disorders, autoimmunity, infectious diseases such as acquired immunodeficiency syndrome, and the engraftment of bone marrow cells to induce tolerance for solid organ, tissue and cellular transplantation.

2. BACKGROUND OF THE INVENTION

A major goal in solid organ transplantation is the permanent engraftment of the donor organ without a graft rejection immune response generated by the recipient, while preserving the immunocompetence of the recipient against other foreign antigens. Typically, in order to prevent host rejection responses, nonspecific immunosuppressive agents such as cyclosporine, methotrexate, steroids and FK506 are used. These agents must be administered on a daily basis and if stopped, graft rejection usually results. However, a major problem in using nonspecific immunosuppressive agents is that they function by suppressing all aspects of the immune response, thereby greatly increasing a recipient's susceptibility to infections and other diseases, including cancer.

Furthermore, despite the use of immunosuppressive agents, graft rejection still remains a major source of morbidity and mortality in human organ transplantation. Most human transplants fail within 10 years without permanent graft acceptance. Only 50% of heart transplants survive 5 years and 20% of kidney transplants survive 10 years. (See Opelz et al., 1981, Lancet 1: 1223; Gjertson, 1992, UCLA Tissue Typing Laboratory, p. 225; Powles, 1980, *Lancet*, p. 327; Ramsay, 1982, *New Engl. J. Med.*, p. 392). It would therefore be a major advance if tolerance to the donor cells can be induced in the recipient.

The only known clinical condition in which complete systemic donor-specific transplantation tolerance occurs is when chimerism is created through bone marrow transplantation. (See Qin et al., 1989, *J Exp Med.* 169: 779; Sykes et al., 1988, *Immunol. Today* 9: 23; Sharabi et al., 1989, *J. Exp. Med.* 169: 493). This has been achieved in neonatal and adult animal models as well as in humans by total lymphoid irradiation of a recipient followed by bone marrow transplantation with donor cells. The success rate of allogeneic bone marrow transplantation is, in large part, dependent on the ability to closely match the major histocompatibility complex (MHC) of the donor cells with that of the recipient cells to minimize the antigenic differences between the donor and the recipient, thereby reducing the frequency of host-versus-graft responses and graft-versus-host disease (GVHD). In fact, MHC matching is essential, only one or two antigen mismatch is acceptable because GVHD is very severe in cases of greater disparities. In addition, it also requires the appropriate conditioning of the recipient by lethal doses of total body irradiation (TBI).

The MHC is a gene complex that encodes a large array of individually unique glycoproteins expressed on the surface of both donor and host cells that are the major targets of a transplantation rejection immune responses. In the human, the MHC is referred to as HLA. When HLA identity is achieved by matching a patient with a family member such as a sibling, the probability of a successful outcome is relatively high, although GVHD is still not completely eliminated. However, when allogeneic bone marrow transplantation is performed between two MHC-mismatched individuals of the same species, common complications involve failure of engraftment, poor immunocompetence and a high incidence of GVHD. Unfortunately, only about 20% of all potential candidates for bone marrow transplantation have a suitable family member match.

The field of bone marrow transplantation was developed originally to treat bone marrow-derived cancers. It is believed by those skilled in the art even today that lethal conditioning of a human recipient is required to achieve successful engraftment of donor bone marrow cells in the recipient. In fact, prior to the present invention, current conventional bone marrow transplantation has exclusively relied upon lethal conditioning approaches to achieve donor bone marrow engraftment. The requirement for lethal irradiation of the host which renders it totally immunocompetent poses a significant limitation to the potential clinical application of bone marrow transplantation to a variety of disease conditions, including solid organ or cellular transplantation, sickle cell anemia, thalassemia and aplastic anemia.

The risk inherent in tolerance-inducing conditioning approaches must be low when less toxic means of treating rejection are available or in cases of morbid, but relatively benign conditions. In addition to solid organ transplantation, hematologic disorders, including aplastic anemia, severe combined immunodeficiency (SCID) states, thalassemia, diabetes and other autoimmune disease states, sickle cell anemia, and some enzyme deficiency states, may all significantly benefit from a nonlethal preparative regimen which would allow partial engraftment of allogeneic or even xenogeneic bone marrow to create a mixed host/donor chimeric state with preservation of immunocompetence and resistance to GVHD. For example, it is known that only approximately 40% of normal erythrocytes are required to prevent an acute sickle cell crisis (Jandl et al., 1961, Blood 18(2): 133; Cohen et al., 1984, Blood 76(7): 1657), making sickle cell disease a prime candidate for an approach to achieve mixed multilineage chimerism. Although the morbidity and mortality associated with the conventional full cytoreduction currently utilized for allogeneic bone marrow transplantation cannot be justified for relatively benign disorders, the induction of multilineage chimerism by a less aggressive regimen certainly remains a viable option. Moreover, the use of bone marrow from an HIV-resistant species offers a potential therapeutic strategy for the treatment of acquired immunodeficiency syndrome (AIDS) if bone marrow from a closely related species will also engraft under similar non-lethal conditions, thereby producing new hematopoietic cells such as T cells which are resistant to infection by the AIDS virus.

A number of sublethal conditioning approaches in an attempt to achieve engraftment of allogeneic bone marrow stem cells with less aggressive cytoreduction have been reported in rodent models (Mayumi and Good, 1989, J Exp Med 169: 213; Slavin et al., 1978, J Exp Med 147(3): 700; McCarthy et al., 1985, Transplantation 40(1): 12; Sharabi et al., 1990, J Exp Med 172(1): 195; Monaco et al., 1966, Ann NY Acad Sci 129: 190). However, reliable and stable donor cell engraftment as evidence of multilineage chimerism was not demonstrated, and long-term tolerance has remained a question in many of these models (Sharabi and Sachs, 1989, J. Exp. Med. 169: 493; Cobbold et al., 1992, Immunol. Rev. 129: 165; Qin et al., 1990, Eur. J. Immunol. 20: 2737). Moreover, reproducible engraftment has not been achieved, especially when multimajor and multiminor antigenic disparities existed.

Permanent tolerance to donor antigens has been documented in H-2 (MHC) identical or congenic strains with minimal therapy and/or transplantation of donor skin drafts or splenocytes alone (Qin et al., 1990, Eur J Immunol 20: 2737). However, similar attempts to achieve engraftment and tolerance in MHC-mismatched combinations have not enjoyed the same success. In most models, only transient donor-specific tolerance has been achieved (Mayumi et al., 1987, Transplantation 44(2): 286; Mayumi et al., 1986, Transplantation 42(4): 417; Cobbold et al., 1990, Eur J Immunol 20: 2747; Cobbold et al., 1990, Seminars in Immunology 2: 377).

Early work by Wood and Monaco attempted to induce tolerance using bone marrow plus anti-lymphocyte serum (ALS) in partial MHC-matched donor-recipient combinations (Wood et al., 1971, Trans Proc 3(1): 676; Wood and Monaco, 1977, Transplantation (Baltimore) 23: 78). Even in this semi-allogeneic system, $F_1$ splenocytes were required to facilitate the induction of tolerance, and thymectomy was required for stable long-term tolerance. The additional requirement for splenocytes and thymectomy made potential clinical applicability of such an approach unlikely. However, these studies identified two key factors required for the induction of tolerance: an antigenic source of tolerogen, which is not only involved in tolerance induction, but must also be present at least periodically for permanent antigen-specific tolerance, and a method to tolerize, or prevent activation of new T cells from the thymus, i.e. thymectomy, or intrathymic clonal deletion.

Attempts to induce tolerance to allogeneic bone marrow donor cells using combinations of depleting and non-depleting anti-CD4 and CD8 monoclonal antibodies (mAb) resulted in only transient tolerance to MHC-compatible combinations (Cobbold et al., 1992, Immunol Rev 129: 165; Qin et al., 1990, Eur J Immunol 20: 2737). 6Gy of TBI was required to obtain stable engraftment and tolerance when MHC-disparate bone marrow was utilized (Cobbold et al., 1986, Transplantation 42: 239). Sharabi and Sachs attributed the failure of anti-CD4/CD8 mAb therapy alone to the inability of mAb to deplete T cells from the thymus, since persistent cells coated with mAb could be identified in this location (Sharabi and Sachs, 1989, J Exp Med 169: 493). However, subsequent attempts to induce tolerance by the addition of 7Gy of selective thymic irradiation prior to donor bone marrow transplantation also failed. Engraftment was only achieved with the addition of 3Gy of recipient TBI. Therefore, there remains a need for non-lethal methods of conditioning a recipient for allogeneic bone marrow transplantation that would result in stable mixed multilineage allogeneic chimerism and long-term donor-specific tolerance.

3. SUMMARY OF THE INVENTION

The present invention relates to non-lethal methods of conditioning a recipient for bone marrow transplantation. These methods include the use of non-lethal doses of irradiation, cell type-specific antibodies and active fragments thereof, cytotoxic drugs or a combination thereof.

The invention is based, in part, on the Applicant's discovery that treatment of normal mice with non-lethal doses of TBI permits the engraftment of allogeneic bone marrow cells in virtually all recipients. In addition, the dosage of TBI can be further reduced when used in combination with anti-lymphocyte globulin (ALG) or an alkylating agent such as cyclophosphamide (CyP). The dosage of TBI can be reduced even more if it is used with both ALG and CyP, agents with different mechanisms of action and non-overlapping toxicities. The reconstituted animals exhibit stable mixed multilineage chimerism in their peripheral blood containing both donor and recipient cells of all lymphohematopoietic lineages, including T cells, B cells, natural killer (NK) cells, macrophages, erythrocytes and platelets. Furthermore, the mixed allogeneic chimeras display donor-specific tolerance to donor-type skin grafts, while they readily reject third-party skin grafts. Donor-specific tolerance is confirmed also by in vitro assays in which lymphocytes obtained from the chimeras are shown to have diminished proliferative and cytotoxic activities against allogeneic donor cells, but retain normal immune reactivity against third-party cells. All allogeneic chimeras conditioned by non-lethal means survive long-term, maintain stable chimerism and do not manifest symptoms of GVHD.

The working examples further demonstrate that total lymphoid irradiation (TLI), a less aggressive and cytoablative regimen than TBI, may also be used at non-lethal doses to condition non-human primates prior to allogeneic or xenogeneic bone marrow transplantation. TLI may be used most effectively with agents such as CyP, and/or ALG, upon optimizing engraftment with a strategy to minimize toxicity to the recipient.

The hematopoietic microenvironment plays a major role in the engraftment of hematopoietic stem cells. In addition to being a source of growth factors and cellular interactions for the survival and renewal of stem cells, it may also provide physical space for these cells to reside. A number of cell types collectively referred to as stromal cells are found in the vicinity of the hematopoietic stem cells in the bone marrow microenvironment. These cells include both bone marrow-derived $CD45^+$ cells and non-bone marrow-derived $CD45^-$ cells, such as adventitial cells, reticular cells, endothelial cells and adipocytes.

Recently, the Applicant has identified another bone marrow-derived cell type known as hematopoietic facilitatory cells, which when co-administered with donor bone marrow cells enhance the ability of the donor cells to stably engraft in allogeneic and xenogeneic recipients. The facilitatory cells and the stromal cells occupy a substantial amount of space in a recipient's bone marrow microenvironment, which may present a barrier to donor cell engraftment. Hematopoietic stem cells bind to facilitatory cells in vitro and in vivo. Thus, the facilitatory cells may provide physical space or niche on which the stem cells survive and are nurtured. It is therefore desirable to develop conditioning regimens to specifically target and eliminate these and other stromal cell populations in order to provide the space necessary for the hematopoietic stem cells and the associated facilitatory cells in a donor cell preparation to engraft without the use of lethal irradiation.

A wide variety of uses are encompassed by the invention described herein, including, but not limited to, the conditioning of recipients by non-lethal methods for bone marrow transplantation in the treatment of diseases such as hematologic malignancies, infectious diseases such as AIDS, autoimmunity, enzyme deficiency states, anemias, thalassemias, sickle cell disease, and solid organ and cellular transplantation.

4. BRIEF DESCRIPTION OF THE DRAWINGS

FIG. 1 Percentage of animals which engrafted with allogeneic or xenogeneic bone marrow as a function of TBI dose. Lymphoid chimerism was assessed by flow cytometry 2 months post reconstitution. Donor chimerism as low as 0.5% can be detected using this method. Data points represent results for 8 to 20 recipients pooled from 2 to 5 experiments.

Figure 2:
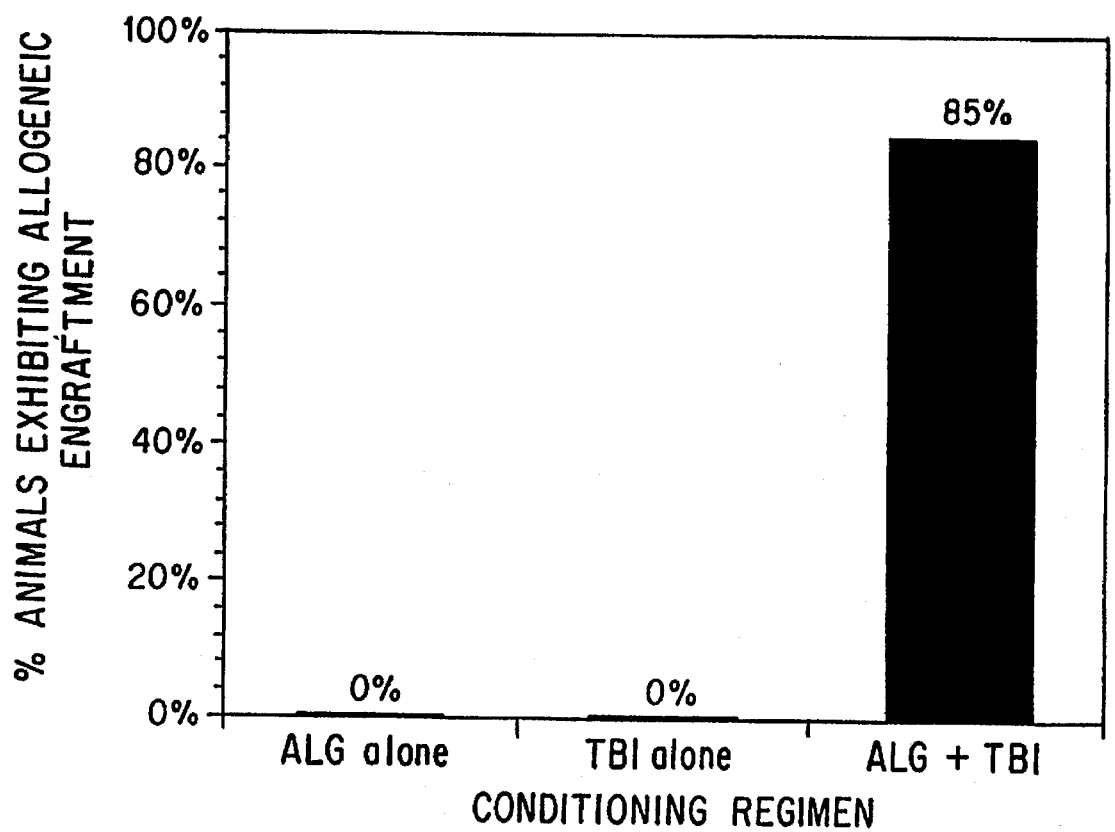

FIG. 2 Percent of animals with allogeneic engraftment in mice treated with one of three conditioning approaches prior to allogeneic bone marrow transplantation—ALG alone given three days prior to transplantation (n=4); 5Gy TBI alone given on the day of transplantation (n=6); or a combination of ALG and 5Gy TBI each as administered previously (n=16). Typing of PBL obtained from treated animals 2 months post reconstitution (BALB/c→B10) was performed using anti Class I $H-2^b$-FITC and $H-2^d$-FITC mAb. Analysis was performed in the lymphoid gate and all values were normalized to 100%.

Figure 3:
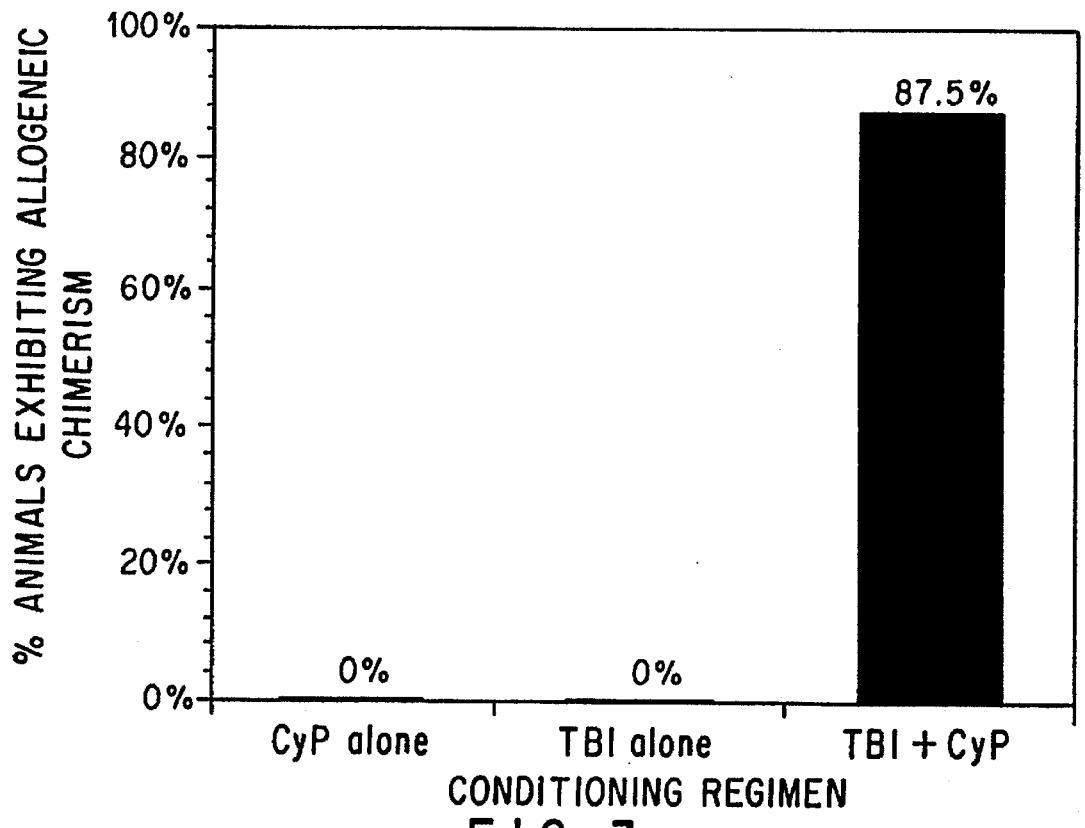

FIG. 3 Percent of animals with allogeneic chimerism in mice treated with one of three conditioning approaches—CyP alone given 2 days prior to bone marrow transplantation (n=5); 5Gy TBI alone on the day of transplantation (n=14); or 5Gy TBI given at the time of marrow transplantation followed 2 days later by CyP (n=8). PBL typing was performed by flow cytometry 2 months post reconstitution (B10.BR→B10 and BALB/c→B10).

Figure 4:
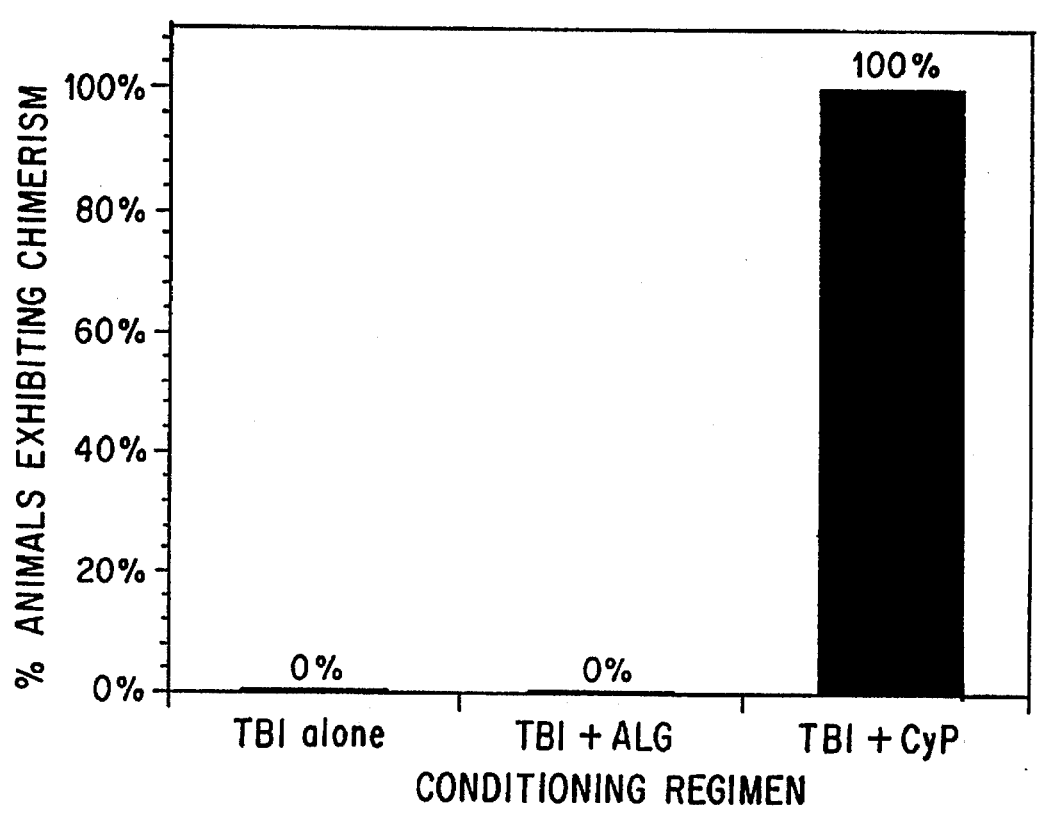

FIG. 4 Percent of mice which engrafted after conditioning with 5Gy TBI given one week prior to BALB/c allogeneic bone marrow transplantation. TBI was administered alone (n=4), followed by ALG given three days prior to bone marrow transplantation (n=4), or followed by CyP given over a four day course prior to transplantation (n=4). Percent of animals which engrafted is represented as a function of the recipient conditioning regimen. PBL typing by flow cytometry was performed to assess donor chimerism in treated animals 2 months after reconstitution. Results are from 1 of 4 representative experiments.

Figure 5:
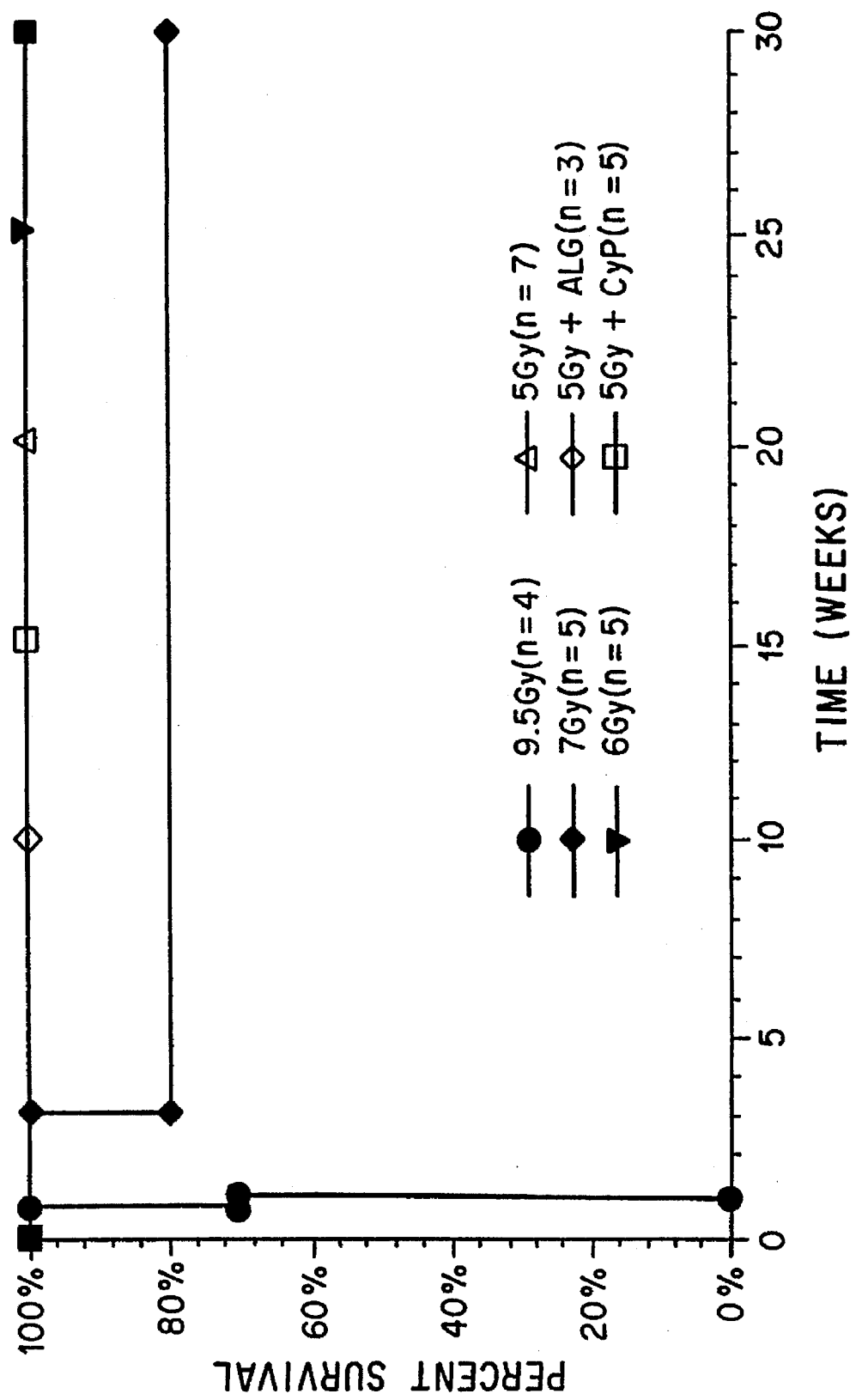
Figure 6G:
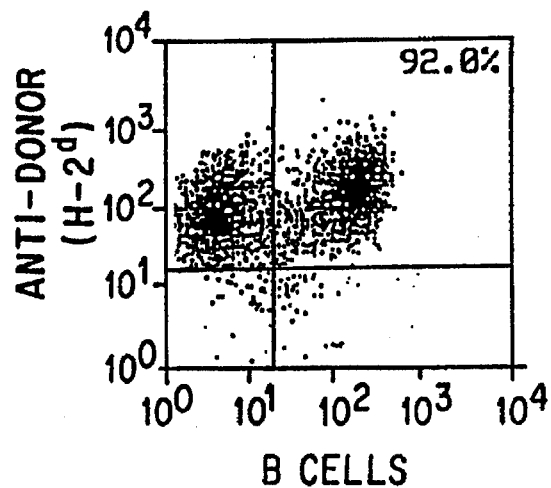
Figure 6H:
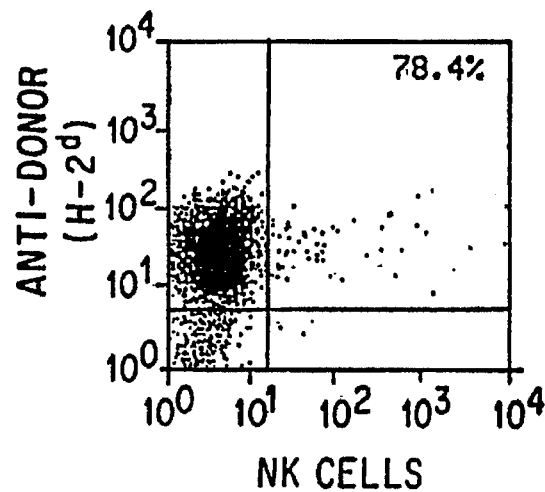
Figure 6I:
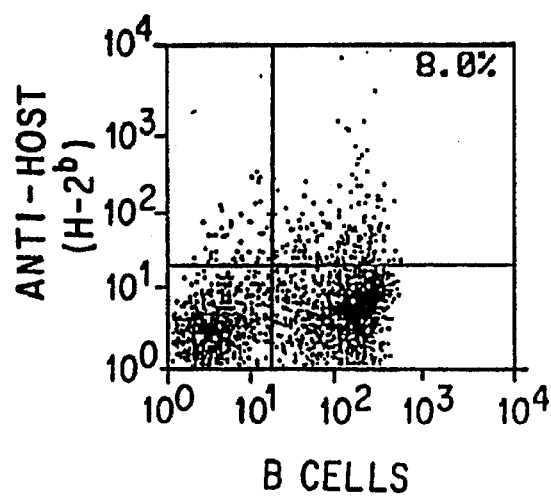
Figure 6J:
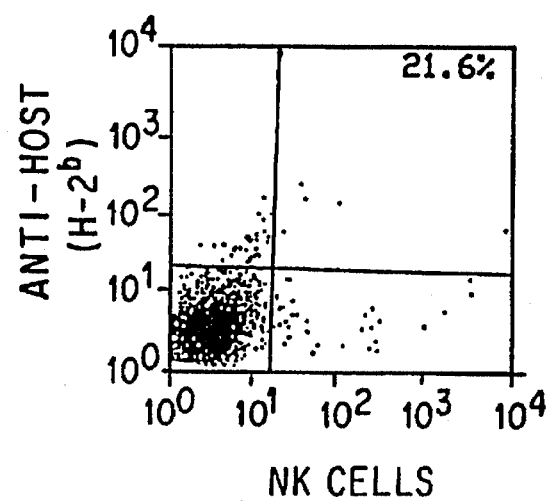
Figure 6K:
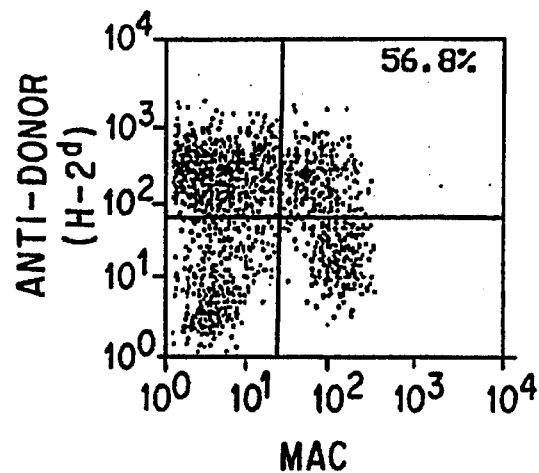
Figure 6L:
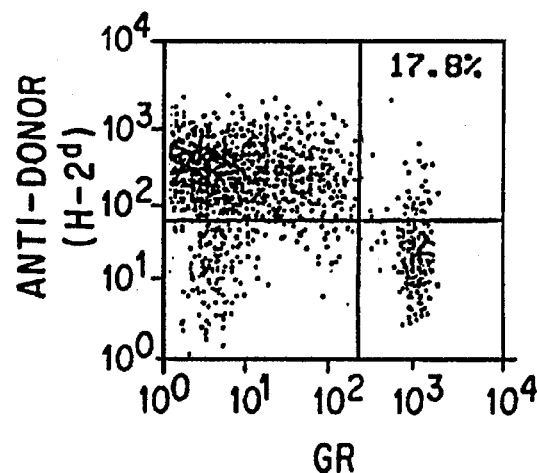
Figure 6M:
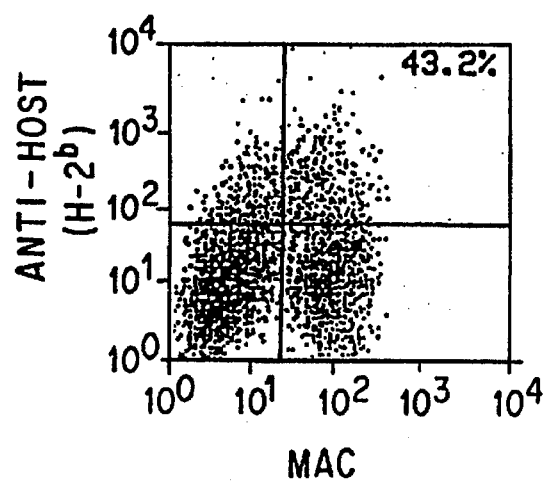
Figure 6N:
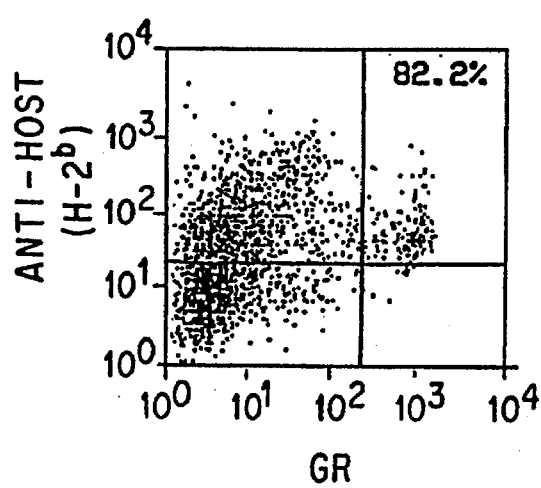

FIG. 5 Life-table survival of untransplanted control mice treated with various nonlethal conditioning regimens. Survival following treatment with 7Gy; 6Gy; 5Gy; 5Gy plus 7 µg/kg ALG i.v.; or 5Gy plus 200 mg/kg CyP i.p. as compared to conventional 9.5Gy lethal irradiation.

FIG. 6A–6J Two-color flow cytometric analysis for the proportion of allogeneic donor-derived lymphoid (T and B cell), NK, and myeloid (macrophage and granulocyte) lineages in a representative mixed allogeneic chimera prepared using a nonlethal conditioning regimen (BALB/c→B10). Splenic lymphoid tissue was analyzed 10–12 weeks following reconstitution.

Recipient ($H-2^b$) and donor-derived ($H-2^d$) cells of lymphoid and NK lineages were analyzed in the lymphoid gate using anti-$H-2^b$ and $H-2^d$ mAb directly conjugated to FITC or biotinylated and detected with a second streptavidin antibody conjugated to PE (SA-PE). The various subsets were analyzed using anti-T lymphocyte mAb ($\alpha\beta$TCR-PE, CD4-FITC, CD8-PE), shown in FIG. 6A–6F, and anti-B lymphocyte (B220-FITC), and anti-natural killer cell (NK1.1-PE) uAb displayed in FIG. 6G–6J. FITC and PE conjugated Leu4 were used as irrelevant controls for background staining for all flow cytometric analysis. The percentage of donor and recipient-derived cells within each lineage is expressed in the upper right hand corner of each respective plot. Results are normalized to 100%.

FIG. 6K–6N Two-color flow cytometric analysis for the proportion of allogeneic donor-derived lymphoid (T and B cell), NK, and myeloid (macrophage and granulocyte) lineages in a representative mixed allogeneic chimera prepared using a nonlethal conditioning regimen (BALB/c→B10). Splenic lymphoid tissue was analyzed 10–12 weeks following reconstitution. Further analysis of recipient and donor-derived myeloid lineages was performed in the myeloid gate using biotinylated anti-H-$2^b$ and H-$2^d$ mAb detected using SA-PE. Macrophages were analyzed using MAC-1 FITC and granulocytes were detected using GR-1 FITC. The percentage of donor and recipient-derived cells within each lineage is expressed in the upper right hand corner of each respective plot. Results are normalized 100%.

Figure 7:
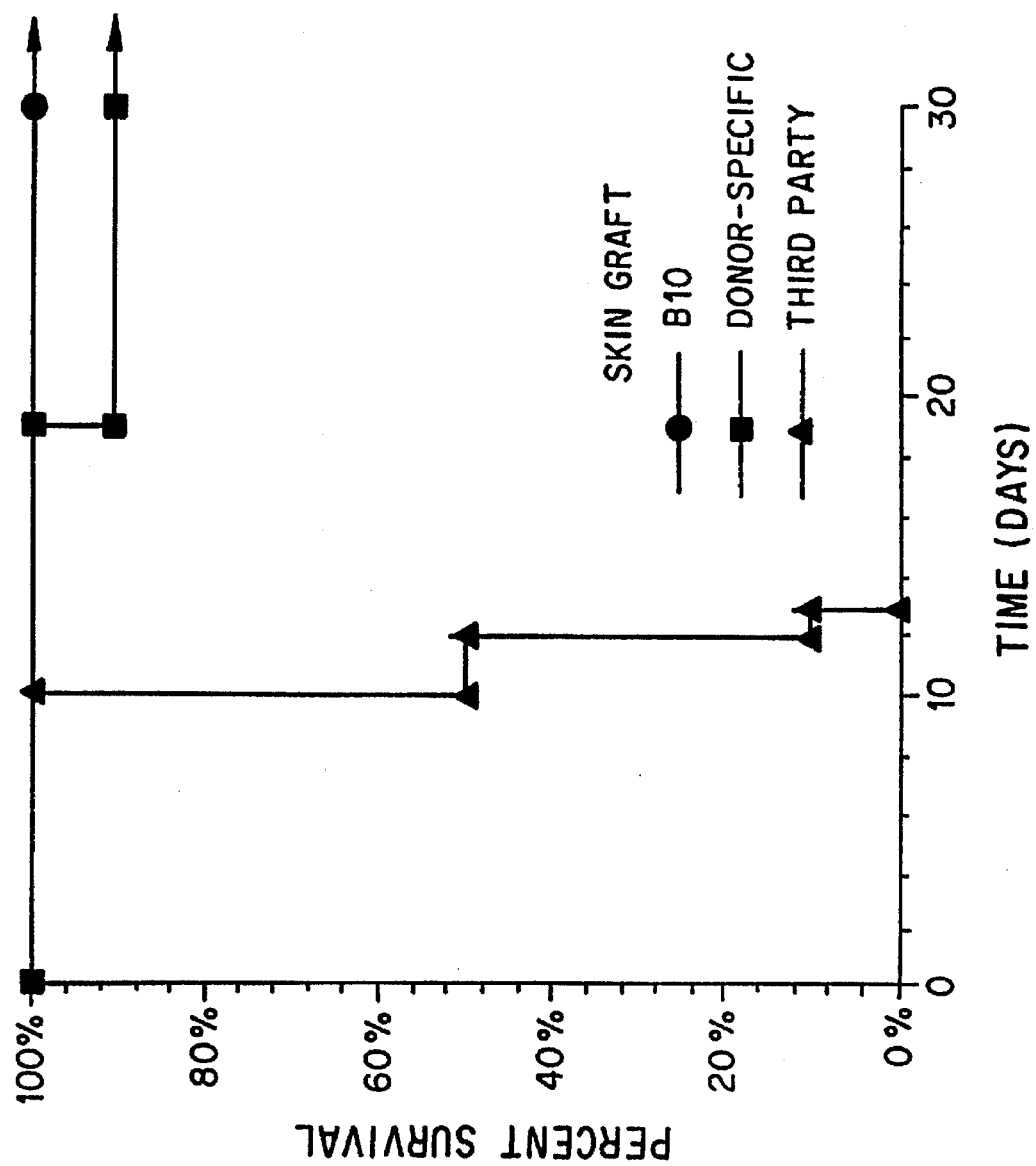

FIG. 7 Survival of full thickness tail skin grafts placed 1 to 7 months post reconstitution using two different donor strain combinations B10.BR (H-$2^k$) or BALB/c (H-$2^d$). Each animal (n=14) received three skin grafts: recipient-type (B10; H-$2^b$); donor-type (B10.BR; H-$2^k$, or BALB/c; H-$2^d$; and third party (DBA; H-$2^d$ or B10.BR; H-$2^k$). Survival was calculated by the life table method. Grafts were followed for a minimum of 35 days. Grafts were scored for evidence of rejection, which was considered complete when no viable residual could be detected.

Figure 8A:
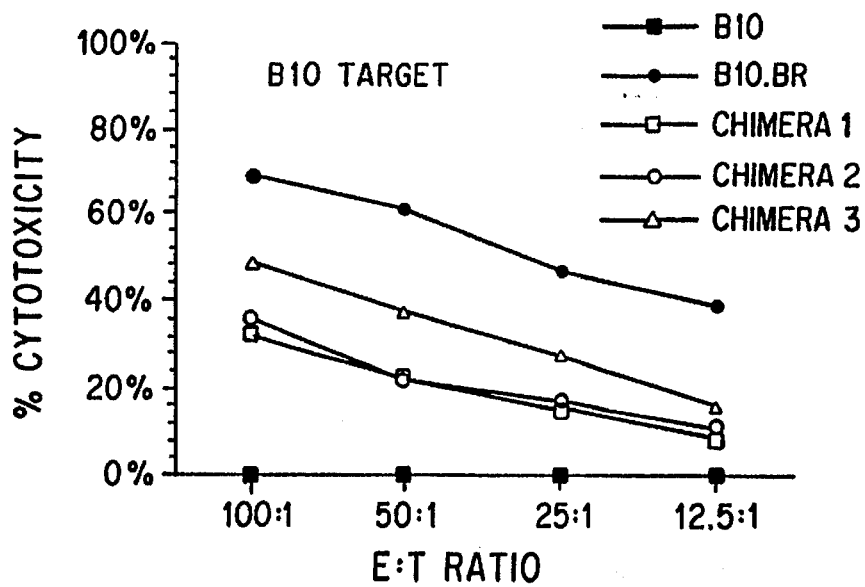
Figure 8B:
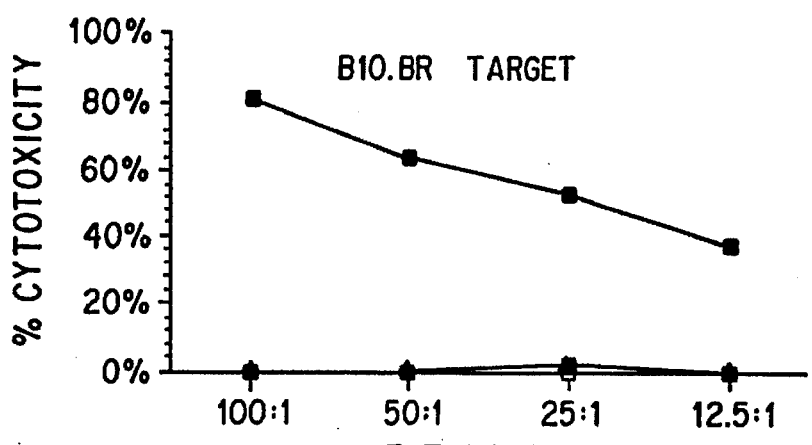
Figure 8C:
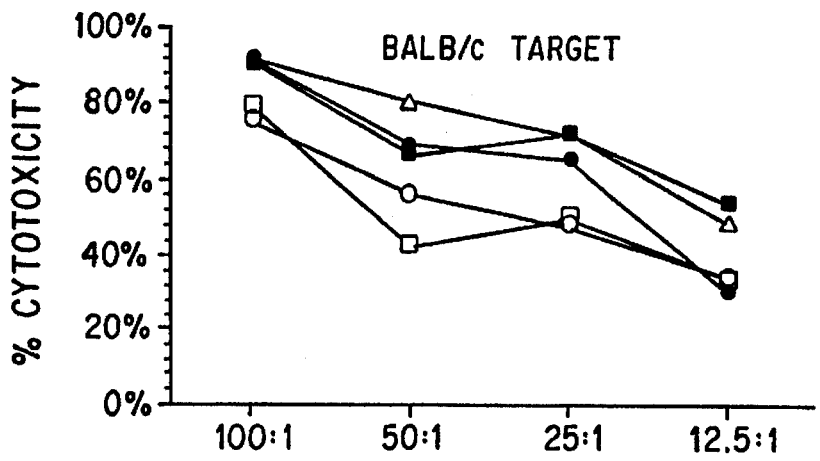

FIG. 8A–8C Specific CTL lysis of $^{51}$Cr-labelled target in one-way CML towards recipient (B10), donor (B10.BR), and third-party (BALB/c) targets. Spontaneous release was <25% unless otherwise indicated. One of five representative experiments.

Figure 9:
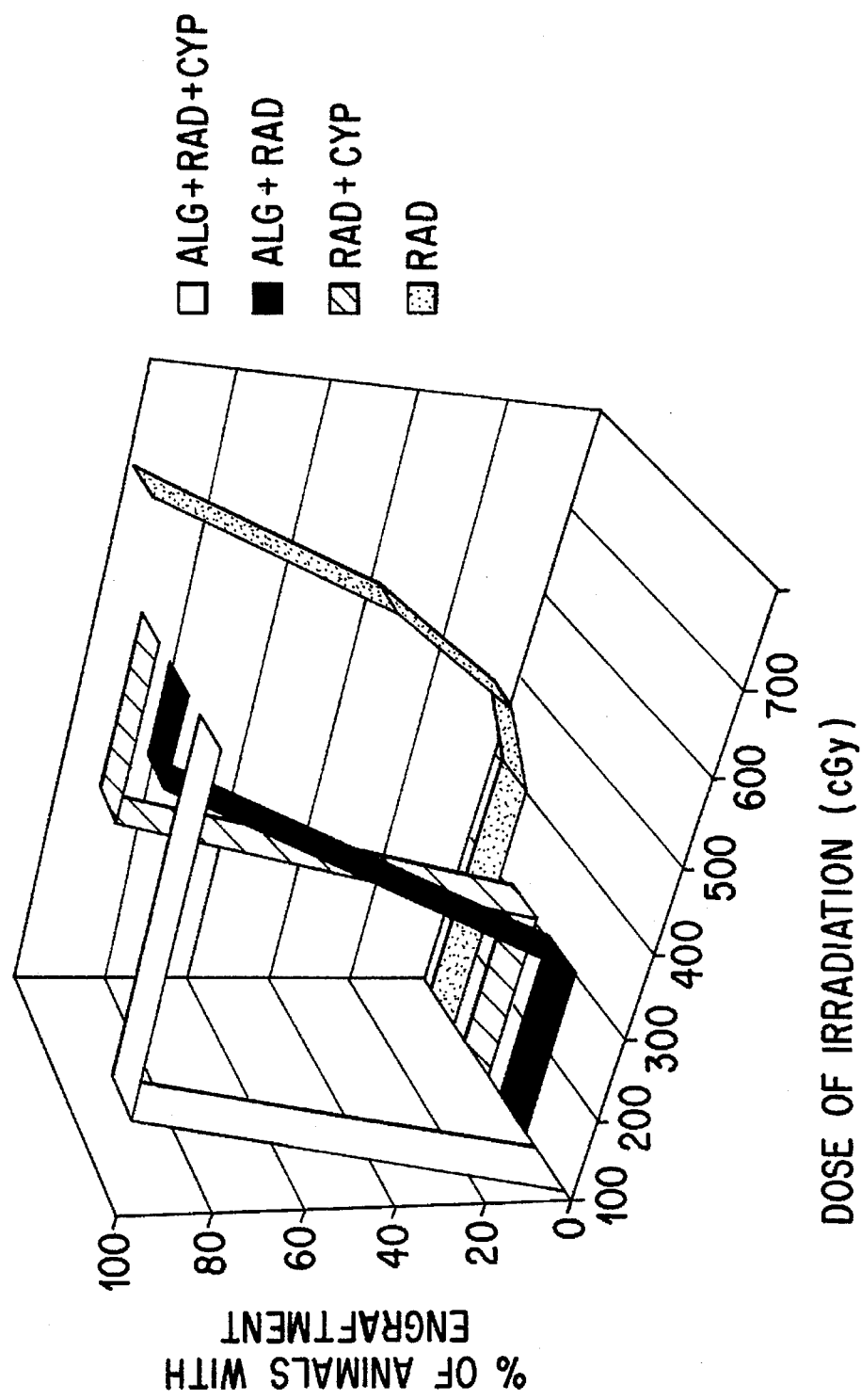

FIG. 9 Percentage of animals with allogeneic donor cell engraftment after treatment with various cytoablative agents.

Figure 10:
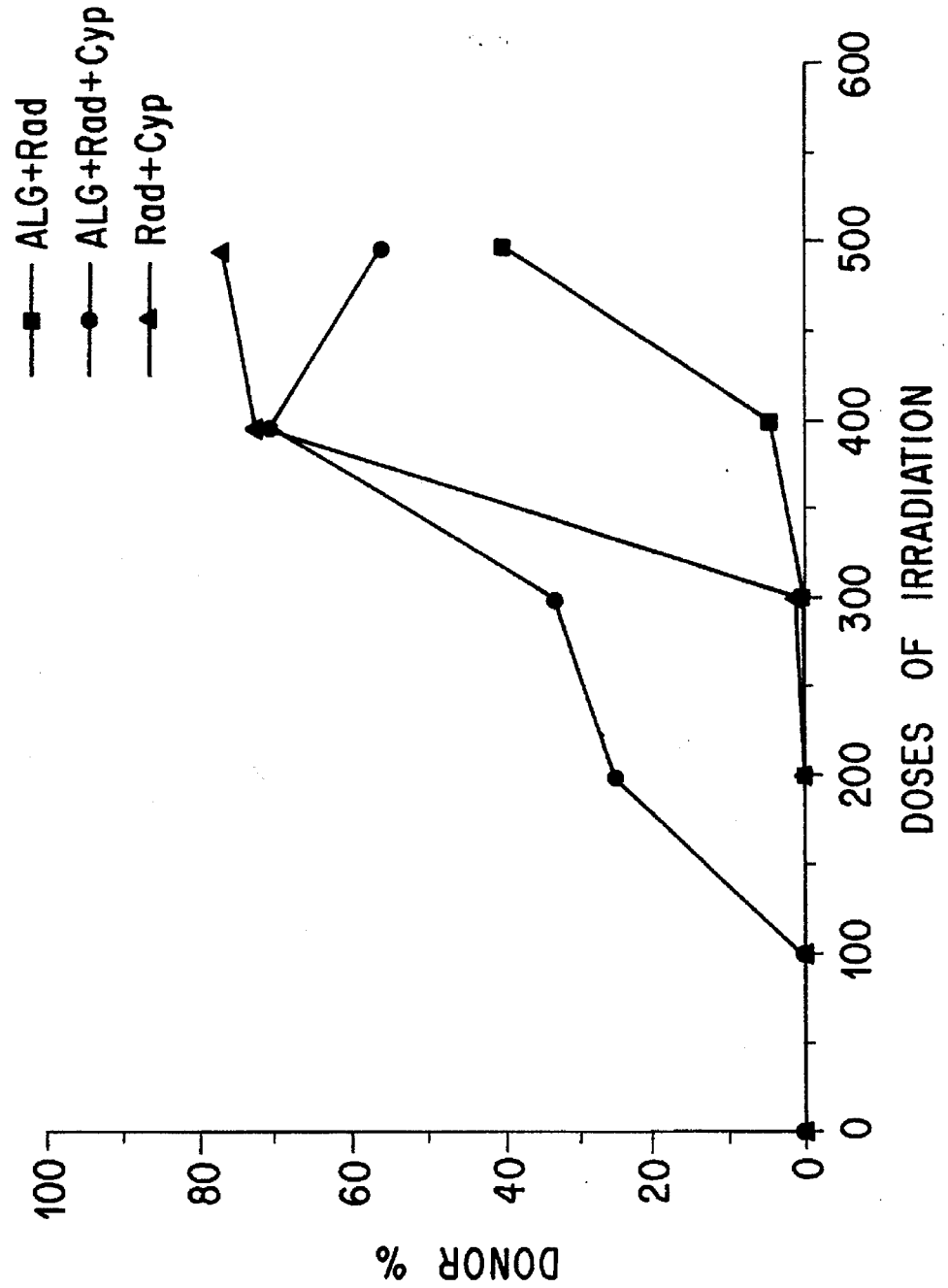

FIG. 10 Percentage of donor cell engraftment in mice engrafted with allogeneic bone marrow cells after treatment with CyP, ALG and various doses of TBI. B10 mice were transplanted with 15×10$^6$ B10.BR cells.

Figure 11:
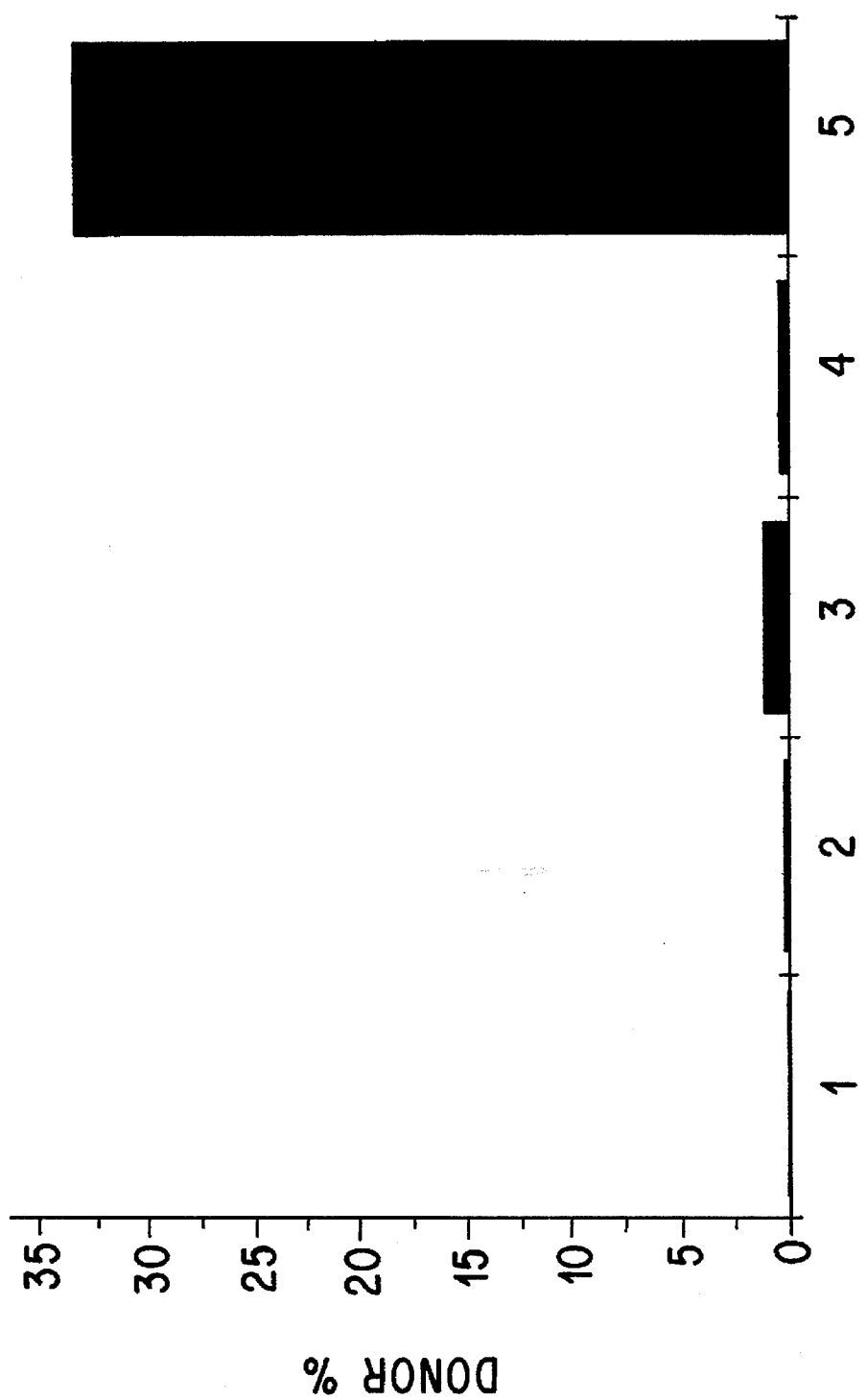

FIG. 11 Percentage of allogeneic donor cell engraftment in mice treated with: 1=3Gy TBI, 2=ALG (2 mg)+3Gy TBI, 3=3Gy TBI+CyP (200 mg/kg), 4=ALG (2 mg)+CyP (200 mg/kg), 5=ALG (2 mg)+3Gy TBI+CyP (200 mg/kg)

5. DETAILED DESCRIPTION OF THE INVENTION

The present invention relates to non-lethal methods of conditioning a recipient for bone marrow transplantation. These methods include the use of non-lethal doses of irradiation, cell type-specific antibodies and active fragments thereof, cytotoxic drugs or a combination thereof. In particular, the present invention encompasses an approach to make space in a recipient's bone marrow by targeting critical cell populations in the hematopoietic microenvironment in the complete absence of radiation treatment.

The invention is discussed in more detail in the subsections below, solely for the purpose of description and not by way of limitation. For clarity of discussion, the specific procedures and methods described herein are exemplified using animal models; they are merely illustrative for the practice of the invention. Analogous procedures and techniques are equally applicable to all mammalian species, including human subjects.

5.1. NON-LETHAL CONDITIONING REGIMENS FOR DONOR CELL ENGRAFTMENT

Mixed allogeneic chimerism has been demonstrated to be an effective means to induce donor-specific transplantation tolerance and preserve immunocompetence. Unlike fully allogeneic chimeras, which are relatively immunoincompetent, mixed allogeneic chimeras in which both host and donor-derived bone marrow cells co-exist, exhibit superior immunocompetence because of the presence of both host and donor-derived cells (Singer et al., 1981, *J Exp Med* 1-3: 1286; Ildstad et al., 1985, *J Exp Med* 162: 231). Mixed chimerism has been achieved using two different approaches, (1) high dose total lymphoid irradiation (TLI) followed by donor bone marrow transplantation (Slavin et al., 1978, *J Exp Med* 147(4): 963) or (2) total body irradiation (TBI) followed by the transplantation of a mixture of T-cell depleted syngeneic and allogeneic bone marrow cells (Singer et al., 1981, *J Exp Med* 1-3: 1286; Ildstad et al., 1985, *J Exp Med* 162: 231). Both approaches result in stable long-term syngeneic and allogeneic chimerism and are associated with donor specific transplantation tolerance to skin and solid organ grafts (Ildstad and Sachs, 1984, *Nature* 307: 168). The application of mixed allogeneic chimerism to induce tolerance clinically has been significantly hampered, however, by the excessive morbidity and cytoreduction which is believed to be a prerequisite for allogeneic engraftment across multimajor histocompatibility barriers.

Both host and donor factors are known to influence engraftment. Stable engraftment requires the host to "tolerate" the allogeneic stem cell and provide hematopoietic niches for the allogeneic stem cells to engraft, proliferate, and differentiate. These two conditions, believed to be essential for the engraftment of the stem cell, are referred to as (1) immunosuppression and (2) cytoreduction (Cobbold et al., 1992, *Immunol Rev* 129: 165). Radiation-based regimens optimize both of these requirements by removing radiosensitive components within the recipient bone marrow to "make space" and by providing a generalized immunosuppression.

The efficacy and necessity of TBI in the facilitation of bone marrow engraftment have been demonstrated in a number of syngeneic and allogeneic models (Down et al., 1991, *Blood* 77(3): 661). In earlier studies by Down et al, even syngeneic engraftment failed to occur in a murine model without some pretreatment of the recipient with TBI (Down et al., 1991, *Blood* 77(3): 661). Minimal space and suppression were required for syngeneic reconstitution since partial engraftment occurred with as little as 2Gy. However, significantly greater immunosuppression and/or "hematopoietic space" was required for MHC identical but minor antigen mismatched allogeneic marrow, resulting in failure of engraftment with less than 5.5Gy of TBI (Down et al., 1991, *Blood* 77(3): 661). The dose-response curve of engraftment versus radiation dose in these previous MHC-compatible studies was sigmoidal, with a steep increase in the percentage of allogeneic engraftment seen at doses of 6 Gy or greater. The immunologic resistance to MHC-compatible allogeneic engraftment is nearly identical to the sigmoidal dose-response curve seen for MHC-disparate bone marrow engraftment in the present radiation-based conditioning model for both allogeneic and xenogeneic combinations (FIG. 1). The percentage of animals which engraft with a given radiation dosage undergoes an abrupt transition from no alloengraftment to nearly complete allochimerism within a very precise and reproducible range of 5.5Gy to 7Gy of TBI. The curve is shifted slightly to the right for xenoengraftment. These data therefore support the concept that there is a form of "space-making" provided by irradiation treatment, since at 5.5Gy only 10% of animals engrafted while at 6Gy≧60% engrafted. A difference of 0.5Gy would be unlikely to represent a differential immunosuppressive effect, since NK cells and lymphocytes have a low threshold of radiosensitivity.

There is a well-characterized relative resistance to engraftment of the bone marrow stem cell across allogeneic disparities (Vallera and Blazer, 1989, *Transplantation* 47: 70-1). Three times more allogeneic bone marrow cells are required to achieve reliable engraftment compared with autologous or syngeneic reconstitution (Ildstad and Sachs, 1984, *Nature* 307: 168). Resistance to engraftment is further increased in donor-recipient strain combinations in which both MHC and minor antigen disparities exist and even further for xenoengraftment; i.e. Rat→mouse is eight times more, and human→mouse is ten times more (Ildstad et al., 1991, *J. Exp. Med.* 174: 467). In the present invention, engraftment of MHC and minor antigen-disparate bone marrow occurred less often than did engraftment of MHC-disparate but minor antigen congenic bone marrow in recipients conditioned with a similar dose of TBI. These data indicate that the radioresistance of the barrier to alloengraftment increases with increasing antigenic disparity.

It has been established in Section 6, infra, that alloengraftment can be maximized yet recipient morbidity and mortality minimized by the addition of ALG or CyP to radiation-based conditioning. When 5Gy of TBI was administered in combination with either ALG or CyP, stable engraftment of allogeneic donor bone marrow cells was achieved. However, immunosuppression alone, without TBI, or TBI alone at a dose of 5Gy, were not sufficient for alloengraftment. Furthermore, CyP was equally effective in enhancing allogeneic engraftment when given before or shortly after bone marrow transplantation, in conjunction with low dose TBI. When ALG and CyP are used in combination with TBI, the dosage of TBI necessary to achieve stable donor cell engraftment is substantially reduced to 2Gy or lower. At 3 Gy, there is significant and stable engraftment in most recipients conditioned by the combination treatment.

TBI may be administered in a modified manner in the form of TLI. TLI is delivered in the same fashion as TBI, except that the entire body of the recipient is not exposed. The irradiation is directed at lymphoid tissues such as the spleen, vertebral column, sternum, ribs, etc. As a result, TLI is, in essence, a partial TBI that is less aggressive and cyto-ablative, and thus higher doses may be administered without lethal effects. TLI conditioning may be supplemented by CyP and/or ALG. These agents may be given before or after TLI. Preferably, they should be administered prior to TLI, and at one or more doses.

Historically, TLI has been utilized in fractionated doses to treat cancer patients. Typically, about 20Gy is administered in approximately 10 divided doses at 2Gy/dose. However, a single and relatively high (≧7.5 Gy) dose of TLI as a conditioning regimen has not been studied for conditioning recipients. Section 8, infra, shows that a single dose of TLI may lead to low levels of donor cell engraftment in a small percentage of recipients. However, the combined use of TLI with an alkylating agent such as CyP results in up to 30% of donor cell engraftment in baboons, demonstrating in vivo efficacy in non-human primates. Similarly, TLI may also be used with an antibody such as ALG or an antibody that is directed to stromal cells. The combined use of TLI, antibody and alkylating agent may further reduce the necessary dose of TLI.

The importance of the hematopoietic niches or "space" contributed by the low dose of TBI is even more evident when TBI is given one week prior to bone marrow transplantation, since engraftment did not occur in that setting. This failure to engraft is probably not due to loss of the immunosuppressive effect of the radiation, since suppression of T cell function following a single dose of radiation has been demonstrated to persist for months or even years (Haas et al., 1985, *Trans Proc* 17(1): 1294). Rather, it is highly likely that the making of space is a prerequisite for engraftment and the delay between TBI and transplantation allowed the host marrow to undergo radiation repair, occupy the available spaces created by the radiation, and prevent alloengraftment despite adequate immunosuppression by ALG. Repair of sub-lethal damage, resulting in a similar dose-sparing effect, has been documented with fractionated TBI in syngeneic and MHC-compatible models (Down et al., 1991, *Blood* 77(3): 661). This repair results in a greater resistance to alloengraftment with a shift in the radiation dose-response curve requiring an additional 3Gy of initial radiation to induce donor chimerism (Down et al., 1991, *Blood* 77(3): 661).

It is of note that the same failure of alloengraftment did not occur if TBI is given one week prior to allogeneic bone marrow transplantation and followed by CyP treatment. Unlike ALG, which is believed to be immunosuppressive but not cytoreductive, CyP is toxic to rapidly proliferating cells. This toxicity may, therefore, have prevented the repair of sublethal damage to hematopoietic niches and syngeneic repopulation necessary to resist alloengraftment. In addition, CyP has been shown to result in endothelial injury with subsequent loss in the integrity of the sinus endothelial barrier (Shirota and Tavassoli, 1991, *Exp. Hematol.* 19: 369). The augmentation of donor chimerism seen with CyP, as compared to ALG, therefore, may be secondary to increased access to hematopoietic niches rather than to any increase in the amount of unoccupied space.

The induction of tolerance towards MHC-disparate grafts using mAb therapy was recently reported (Cobbold et al., 1990, *Eur J Immunol* 20: 2747). However, tolerance to other tissues of donor organ, i.e. splenocytes or bone marrow, was not reliably induced without the addition of 6Gy TBI. Moreover, engraftment was variable and often transient. This disparity in tolerance for different tissues has been termed "split tolerance". These recipients exhibit "tolerance" towards a local form of donor antigen, i.e. skin graft, but often exhibit proliferative and cytotoxic reactivity to other donor tissues such as lymphoid cells.

Although split tolerance has been a limitation in several nonlethal conditioning regimens, the preparation of allogeneic chimeras using low dose TBI-regimens in the present invention have resulted in systemic donor-specific tolerance towards both skin grafts and lymphoid tissues of donor-type. The prolonged survival of donor-type skin grafts in all animals which exhibit successful engraftment of allogeneic bone marrow is donor-specific, since chimeras are immunocompetent to reject third-party skin grafts with a time course similar to unmanipulated control mice. Similarly, animals which exhibit any degree of donor chimerism also exhibit specific functional tolerance in vitro towards donor antigens on lymphoid tissues as assessed by in vitro assays. No evidence of split tolerance has been found in any of the allogeneic chimeras tested, as animals which fail to exhibit tolerance towards donor lymphoid tissues also reject donor skin grafts and contain no detectable donor chimerism. In the present invention, chimerism is always associated with stable functional donor-specific transplantation tolerance in vivo and in vitro.

The mixed chimeras prepared with the nonlethal approaches characterized in the studies described herein exhibit similar multilineage donor chimerism which is stable for the duration of follow-up ($\geq 8$ months). Significant levels of donor chimerism are detected within each of the various lineages including lymphoid (T and B lymphocytes), NK cell, and myeloid (macrophages, granulocytes, erythrocytes, and platelets) in almost all animals examined (n=10). The level of donor chimerism among each of the lineages is variable within individual animals, an observation which parallels the findings in mixed chimeras prepared with lethal conditioning. These data suggest that tight regulatory control over both syngeneic and allogeneic pluripotent stem cells exists which determines the level of production of each individual lineage. Moreover, lineage production is also influenced by the conditioning used, since non-lethal mixed xenogeneic (Rat→mouse) chimeras produced rat-derived red blood cells, while chimeras prepared by lethal conditioning do not. There is also substantial data to suggest that the hematopoietic microenvironment in which the stem cells reside, may profoundly influence the development of the stem cells into various cell lineages.

The specificity of this regulation is clearly evident on examination of those chimeras which produce erythrocytes of only donor origin, despite an intact host hematopoietic system and production of syngeneic cells within the other hematolymphopoietic lineages. Such regulation may require specific cell-cell interactions found within "hematopoietic niches", thereby explaining the necessity of "space-making" agents, such as radiation, in allogeneic marrow transplantation. Recent studies by Jacobsen (Jacobsen et al., 1992, J Exp Med 176: 927) have shown the specific cell-cell interactions within murine bone marrow between B cell precursors and a stromal cell. Each lineage may have a limited number of specific stromal cells necessary for developmental maturation or, alternatively, a single cell may be regulated to favor differentiation of a certain lineage at a given time. Prior to the present invention, methods to specifically target the cells which constitute the hematopoietic niches have not been attempted.

Nonlethal conditioning approaches which result in multilineage mixed chimerism may significantly expand the application of bone marrow transplantation for non-malignant diseases. Hematologic abnormalities including thalassemia and sickle cell disease, autoimmune states, and several types of enzyme deficiency states have previously been excluded from bone marrow transplantation strategies because the high morbidity and mortality associated with conditioning to achieve fully allogeneic bone marrow reconstitution could not be justified (Kodish et al., 1991, N Engl J Med 325(19): 1349). Sickle cell disease is a prime candidate for mixed allogeneic reconstitution since only 40% of normal erythrocytes are required to prevent an acute crisis (Jandl et al., 1961, Blood 18(2):133; Cohen et al., 1992, Blood 76(7): 1657).

In the present invention, multilineage mixed chimerism has been reliably achieved using minimal conditioning of the recipient. Other models of engraftment using sublethal recipient conditioning have failed to establish the presence of stable multilineage mixed allogeneic chimerism and permanent donor-specific tolerance which is crucial for conditions such as sickle cell disease or thalassemia. The nonlethal conditioning approaches described herein, may be useful in the treatment of non-fatal hematologic abnormalities, as well as for the induction of tolerance to simultaneous or subsequent cellular or solid organ allografts, in which the morbidity of conventional full cytoreduction is prohibitive.

5.2. ANTIBODY FOR USE IN CONDITIONING

The hematopoietic microenvironment is primarily composed of hematopoietic cells and stromal cells. The stromal cells occupy much space of the bone marrow environment and they include endothelial cells that line the sinusoids, fibroblastic cells such as adventitial reticular cells, perisinusoidal adventitial cells, periarterial adventitial cells, intersinusoidal reticular cells and adipocytes, and macrophages (Dorshkind, 1990, Annu. Rev. Immunol. 8: 111; Greenberger, 1991, Crit. Rev. Oncology/Hematology 11: 65). In addition, the Applicant has recently identified, characterized and purified a previously unknown cell type from the bone marrow that facilitates the engraftment of bone marrow stem cells across allogeneic and xenogeneic barriers. This cell referred to as hematopoietic facilitatory cell must be matched with the stem cell at the MHC for it to enhance stem cell engraftment. The facilitatory cells express a unique profile of cell surface markers: Thy-1$^+$, CD3$^+$, CD8$^+$, CD45$^+$ CD45R$^+$, MHC class II$^+$, CD4$^-$, CD5$^-$, CD14$^-$, CD16$^-$, CD19$^-$, CD20$^-$, CD56$^-$, $\gamma\delta$-TCR$^-$ and $\alpha\beta$B-TCR$^-$. These cells are a newly recognized stromal cell population that is a critical component of the hematopoietic microenvironment. In allogeneic reconstitution experiments in mice, the murine facilitatory cells have been shown to be radiosensitive at about 3Gy.

The various stromal cell types express a number of well-characterized surface markers, including but not limited to, vascular addressing, mannosyl and galactosyl residues, fasciculin III, villin, tetrapeptide, neural cell adhesion molecule receptor, hemonectin, B1 integrins, B2 integrins and B3 integrins (Greenberger, 1991, Crit. Rev. Oncology/Hematology 11: 65). All the stromal cell populations including the facilitatory cells are potential targets of the conditioning regimen for recipients that is necessary for successful donor cell engraftment. Therefore, antibodies reactive with or specific for stromal cell surface markers may be used to deplete stromal elements in a cell type-specific non-lethal conditioning approach to make space available for bone marrow transplantation. For example, antibodies directed to Thy-1, MHC Class I and Class II molecules expressed on many stromal cell types may be used for this purpose. In addition, a monoclonal antibody designated STRO-1 has been shown to react with a cell surface antigen expressed by stromal elements in human bone marrow (Simmons and Torok-Storb, 1991, Blood 78: 55). This antibody may be particularly useful for depleting stromal cells for making space in the bone marrow. In the mouse model, anti-Thy-1 and rabbit-anti-mouse-brain (RAMB) antibodies are effective in removing the facilitatory cell population from the bone marrow. RAMB is a polyclonal serum prepared by immunizing rabbits with homogenized mouse brain (Auchincloss and Sachs, 1983, Transpl. 36: 436). Human brain also contains a number of epitopes cross-reactive with those expressed by the facilitatory cells. Thus, rabbit-anti-human-brain antibodies have been produced and may be used to remove the facilitatory cells from the hematopoietic microenvironment. However, since murine facilitatory cells have been shown to be radiosensitive at about 3Gy but substantial donor cell engraftment does not occur at radiation doses less than 6Gy as shown herein in Section 6, infra, it is possible that the elimination of stromal cell types other than facilitatory cells is necessary to create the greatest amount of space for optimal donor cell engraftment.

Also within the scope of the invention is the production of polyclonal and monoclonal antibodies which recognize novel antigens expressed by stromal cells including the facilitatory cells of the hematopoietic microenvironment for use as specific agents to deplete these cells.

Various procedures known in the art may be used for the production of polyclonal antibodies to antigens of stromal cells including facilitatory cells. For the production of antibodies, various host animals can be immunized by injection with purified or partially purified stromal cells including but not limited to rabbits, hamsters, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

A monoclonal antibody to antigens of stromal cells may be prepared by using any technique which provides for the production of antibody molecules by continuous cell lines in culture. These include but are not limited to the hybridoma technique originally described by Kohler and Milstein (1975, Nature 256: 495–497), and the more recent human B-cell hybridoma technique (Kosbor et al., 1983, *Immunology Today* 4: 72; Cote et al., 1983, *Proc. Natl. Acad. Sci., USA* 80: 2026–2030) and the EBV-hybridoma technique (Cole et al., 1985, *Monoclonal Antibodies and Cancer Therapy*, Alan R. Liss, Inc., pp. 77–96). Techniques developed for the production of "chimeric antibodies" by splicing the genes from a mouse antibody molecule of appropriate antigen specificity together with genes from a human antibody molecule can be used (e.g., Morrison et al., 1984, *Proc. Natl. Acad. Sci. USA*, 81: 6851–6855; Neuberger et al., 1984, *Nature*, 312: 604–608; Takeda et al., 1985, *Nature* 314: 452–454). Such chimeric antibodies are particularly useful for in vivo administration into human patients to reduce the development of host anti-mouse response. In addition, techniques described for the production of single chain antibodies (U.S. Pat. No. 4,946,778) can also be adapted.

Antibody fragments which contain the binding site of the molecule may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments (*Antibody: A Laboratory Manual*, 1988, Harlow and Lane, Cold Spring Harbor).

5.3. USES OF ANTIBODIES TO STROMAL CELLS

The specific embodiments described in Section 6, infra, demonstrate that non-lethal conditioning of a recipient may be achieved by a reduced dose of TBI. Further, similar results can be obtained by an even lower dose of irradiation when applied in combination with ALG or an alkylating agent. Thus, it is possible to develop a non-lethal conditioning method by totally eliminating the use of radiation or chemotherapeutic agents to and by using antibodies to deplete the critical targets of TBI. A likely target of such an approach is the various stromal cell populations that form the hematopoietic microenvironment. Antibodies directed to cell surface markers of stromal cells may be used to specifically deplete these cells without other adverse side effects in preparing a recipient for bone marrow transplantation in the absence of lethal doses of irradiation. Alternatively, such antibodies may be used in conjunction with low doses of irradiation and/or cytotoxic drugs.

According to this embodiment, the antibodies of the present invention can be modified by the attachment of an antiproliferative or toxic agent so that the resulting molecule can be used to kill cells which express the corresponding antigen (Vitetta and Uhr, 1985, *Annu. Rev. Immunol.* 3: 197–212). The modified antibodies may be used in the preparation of a recipient prior to bone marrow transplantation in order to deplete stromal cells to make space for donor cells to engraft.

Accordingly, the antiproliferative agents which can be coupled to the antibodies of the present invention include but are not limited to agents listed in Table 1, infra, which is derived from Goodman and Gilman, 1990, *The Pharmacological Basis of Therapeutics*, Eighth Edition, Pergamon Press, N.Y., pp. 1205–1207, which is incorporated by reference herein.

Such antibody conjugates may be administered to a human patient prior to or simultaneously with donor cell engraftment. It is preferred that these conjugates are administered intravenously. Although the effective dosage for each antibody must be titrated individually, most antibodies may be used in the dose range of 0.1 mg/kg—20 mg/kg body weight. In cases where sub-lethal doses of irradiation are used, TLI of a human recipient may be administered at 5 to 10 Gy as a single dose or a combined total of 22Gy administered in fractionated doses. Preferably, TLI may be used between 7.5–9.5 Gy. Alternatively, TBI may be administered between 5 Gy and 7 Gy.

TABLE 1

ANTI-PROLIFERATIVE AGENTS WHICH CAN BE COUPLED TO ANTIBODIES

| Class | Type | Agent |
| --- | --- | --- |
| Alkylating Agents | Nitrogen Mustards | Mechlorethamine |
| | | Cyclophosphamide |
| | | Ifosfamide |
| | | Melphalan |
| | | Chlorambucil |
| | Ethylenimine Derivatives | Hexamethyl-melamine |
| | | Thiotepa |
| | Alkyl Sulfonates | Busulfan |
| | Nitrosoureas | Carmustine |
| | | Lomustine |
| | | Semustine |
| | | Streptozocin |
| | Triazenes | Dacarbazine |
| Antimetabolites | Folic Acid Analogs | Methotrexate |
| | Pyrimidine Analogs | Fluorouracil |
| | | Floxuridine |
| | | Cytarabine |
| | Purine Analogs | Mercaptopurine |
| | | Thioguanine |
| | | Pentostatin |
| Natural Products | Vinca Alkaloids | Vinblastine |
| | | Vincristine |
| | Epipodophyllotoxins | Etoposide |
| | | Teniposide |
| | Antibiotics | Dactinomycin |
| | | Daunorubicin |
| | | Doxorubicin |

TABLE 1-continued

ANTI-PROLIFERATIVE AGENTS WHICH CAN BE COUPLED TO ANTIBODIES

| Class | Type | Agent |
|---|---|---|
| | | Bleomycin |
| | | Plicamycin |
| | | Mitomycin |
| | Enzymes | L-Asparaginase |
| Miscellaneous Agents | Platinum | Cisplatin |
| | Coordinated Complexes | Carboplatin |
| | Anthracenedione | Mitoxantrone |
| | Substituted Urea | Hydroxyurea |
| | Methyl Hydrazine Derivative | Procarbazine |
| | Adrenocortical Suppressant | Mitotane Aminoglutethimide |
| Hormones and Antagonists | Adrenocorticosteroids | Prednisone |
| | Progestins | Hydroxyprogesterone caproate |
| | | Medroprogesterone acetate |
| | | Megestrol acetate |
| | Estrogens | Diethylstilbestrol |
| | | Ethinyl estradiol |
| | Antiestrogen | Tamoxifen |
| | Androgens | Testosterone propionate |
| | | Fluoxymesterone |
| Radioactive Isotopes | Phosphorous | Sodium phosphate $^{32}$P |
| | Iodine | Sodium idoine $^{131}$I |
| Toxins | | Ricin A chain |
| | | Diphtheria toxin |
| | | Pseudomonas exotoxin A |

Any method known in the art can be used to couple the antibodies to an antiproliferative agent, including the generation of fusion proteins by recombinant DNA technology (Williams et al., 1987, *Protein Engineering* 1: 493).

6. EXAMPLE: ALLOGENEIC BONE MARROW CELLS ENGRAFT IN RECIPIENTS CONDITIONED BY NON-LETHAL METHODS

6.1. MATERIALS AND METHODS

6.1.1. ANIMALS

Male C57BL/10SnJ (B10), B10.BR, and BALB/c mice 6–8 weeks old were purchased from the Jackson Laboratory, Bar Harbor, Me. Animals were housed in a specific pathogen-free facility at the Biomedical Science Tower at the University of Pittsburgh.

6.1.2. FLOW CYTOMETRY

Recipients were characterized for donor cell engraftment using flow cytometry (FACS II, Becton Dickinson; Mountain View, Calif.) to determine the percentage of peripheral blood lymphocytes bearing H-$2^b$, H-$2^k$, and H-$2^d$ encoded antigens as described (Jeffries et al., 1985, *J Exp Med* 117: 127). Briefly, peripheral blood was collected into heparinized plastic serum vials. 200 μl of Medium 199 (Gibco Laboratories; Grand Island, N.Y.) were added to each vial. After thorough mixing, the suspension was layered over 1.5 ml of room temperature Lymphocyte Separation Medium (LSM) (Organon Teknika; Durham, N.C.) and centrifuged at 37° C. (400g×20 minutes). The buffy coat layer was aspirated from the Medium 199-LSM interface and washed with medium. Lymphocytes were stained for class I antigens with anti-H-$2^b$-FITC (Pharmingen; San Diego, Calif.), anti-H-$2^k$-FITC (Pharmingen), and anti-H-$2^d$-FITC (Pharmingen) monoclonal antibodies (Mab) for 45 minutes at 4° C. Lineage typing was performed by two color flow cytometry using anti-B-cell (B220-FITC, Pharmingen), anti-T cell (αβ-TCR-PE, CD4-FITC, CD8-PE, Pharmingen), anti-natural killer cell (NK1.1-PE, Pharmingen), anti-granulocyte (GR-1-FITC, Pharmingen), and anti-monocyte/macrophage (MAC-1-FITC, Boehringer Mannheim; Indianapolis, Ind.) Mab. These lineage-specific Mab were displayed versus anti-host (H-$2^b$, Pharmingen) and anti-donor (H-$2^d$ or H$2^k$, Pharmingen) Mab conjugated to FITC or were biotinylated and detected with a second streptavidin antibody conjugated to (phycoerythrin PE) (Pharmingen). Analyses were performed using forward and side scatter characteristics for the lymphoid and myeloid gates.

6.1.3. PLATELET ISOLATION

Peripheral blood (0.9ml) was collected into heparinized microcentrifuge vials. The blood was spun for four seconds at the maximal setting (14,000 rpm) of an Eppendorf microcentrifuge (Beckman #5415). This setting was chosen through an optimization strategy in which force and times were varied as a function of retrieved platelet number. This duration included the acceleration phase, which is incomplete when power is curtailed at the four second mark. After this, the samples were allowed to slow to a halt without braking. Platelet-rich plasma was then carefully aspirated with a disposable polyethylene pipette, avoiding any disturbance of the buffy coat. Triplicate platelet counts were obtained using a Coulter Model ZB1 counter (Hialeah, Fla.), and the average (variation 5%) calculated. Platelets were then processed as described for the glucose phosphate isomerase-1 assay, infra.

6.1.4. GLUCOSE PHOSPHATE ISOMERASE-1 (GPI-1) ASSAY

Typing of red blood cell (RBC) and platelet phenotypes was performed using the GPI-1 assay (Ildstad, et al., 1991, *J Exp Med* 174: 467). The precipitation pattern for BALB/c mouse and B10 mouse were performed as controls and determined to be totally disparate. Briefly, 8 μl of RBC were lysed in 400 μl of distilled water, and electrophoresis was performed on a Titan III cellular acetate strips with tris Hcl, 20 mM glycerin, 200 mM buffer (pH 8.7) (200 V for 1 hr.). Application was 2 cm from the anode. After the run, the strips were covered with a 1% agarose gel containing Tris-Hcl 100 Mm (pH 8.0), NADP 300 μM, glucose-6-phosphate dehydrogenase 0.5 U/ml, fructose-6-phosphate 50 Mm, MMT 500 μM and phenozine methosulphate 200 μM. As precipitation occurred with the formation of formazan salt, the bands became visible (blue). The gel was removed, the reaction was arrested by immersing the strips in 5% acetic acid, and the bands were scanned with a Quick-Scan scanner. Percentages were determined by comparison with the positive control. Values for each animal were normalized to 100%. In titrations performed to determine the sensitivity of this assay, as low as 2% of BALB/c RBC titrated into normal B10 RBC could be reliably detected (Ildstad, et al., 1991, *J Exp Med* 174: 467). After isolation, platelets were typed in a similar fashion.

6.1.5. SKIN GRAFTING

Skin grafting was performed by a modification of the method of Billingham and Medawar as previously described (Rappaport, 1977, *Trans Proc* 9: 894; Kunst et al., 1989,

*Immunogenetics* 30: 187). Full thickness skin grafts were harvested from the tails of C57BL/10SnJ (H-2$^b$), B10.BR (H-2$^k$), BALB/C (H-2$^d$), and DBA (H-2$^d$) mice. Mice were anesthetized with 0.1% Nembutal (Abbott Laboratories; North Chicago, Ill.) intraperitoneally and full thickness graft beds were prepared surgically in the lateral thoracic wall. Care was taken to preserve the panniculus carnosum. The grafts were covered by a double layer of vaseline gauze and a plaster cast to prevent shearing. Three skin grafts from syngeneic, allogeneic donor, and third-party animals were placed on each animal with separation of each defect for graft placement by a 3 mm skin bridge. Casts were removed on the eighth day. Grafts were scored daily for percent rejection, and rejection was considered complete when no residual viable graft could be seen. Chronic rejection was the time point at which erythema and induration appeared in the grafts. Graft survivals were calculated by the life-table method (Gehan, 1969, *J Chronic Dis* 21: 629) and the median survival time (MST) was derived from the time point at which 50% of grafts were surviving.

6.1.6. MIXED LYMPHOCYTE REACTIONS (MLR)

Mixed lymphocyte reactions were performed as described (Schwartz et al., 1976, *J Immunol* 116: 929; Hoffman et al., 1990, *J Immunol* 145: 2220). Briefly, murine splenocytes were ACK-lysed (ammonium chloride potassium carbonate lysing buffer), washed, and reconstituted in DMEM (Gibco Laboratories) supplemented with 0.75% normal mouse serum, 0.55 mM L-arginine HCl+13.6 µM folic acid +0.3 mM L-asparagine+10 mM HEPES buffer, 1 mM sodium pyruvate, 2 mM glutamine, 100 U/ml penicillin, 100 µg/ml streptomycin, 0.05 mM 2-mercaptoethanol and 1 mM N$^G$ mono-methyl L-arginine (Hoffman et al., 1990, *J Immunol* 145: 2220 ). 4×10$^5$ responders were stimulated with 4×10$^5$ irradiated stimulators (20Gy) in a total of 200µl of media. Cultures were incubated at 37° C. in 5% CO$_2$ for 4 days, pulsed on the third day with 1 µCi [$^3$H]thymidine (New England Nuclear; Boston, Mass.) and harvested on the fourth day with an automated harvester (MASH II; Microbiological Associated, Bethesda, Md.).

6.1.7. CELL-MEDIATED LYMPHOLYSIS (CML)

CML assays were performed using a modification of techniques as described (Schwartz et al., 1976, *J Immunol* 116: 929; Epstein et al., 1980, *J Immunol* 125: 129; Lang et al., 1981, Trans Proc 13: 1444). RPMI 1640 medium (Gibco Laboratories) was supplemented as above, except that 10% fetal calf serum (Gibco Laboratories) was used in place of normal mouse serum. 4×10$^6$ responders were co-cultured with 4×10$^6$ irradiated splenocyte stimulators (20Gy) in 2 ml of medium at 37° C. for 5 days. Mouse target blasts were stimulated with concanavalin A (Con A) (Miles Yeda Research Products, Rehovot, Israel) for 2–3 days. After 5 days responders were harvested, counted, and resuspended at appropriate effector-to-target ratios with 1×10$^4$ $^{51}$Cr-labeled, 2-3-d Con A mouse splenocyte blasts. After 4.5 hours, supernatants were harvested with the Titertek supernatant harvesting system and specific lysis was calculated as follows: specific lysis=(experimental release–spontaneous release)/(maximal Hcl release–machine background)×100. Spontaneous release was <25% of maximum release unless otherwise indicated.

6.2. RESULTS

6.2.1. ALLOGENEIC ENGRAFTMENT WITH NONLETHAL TOTAL BODY IRRADIATION ALONE: DOSE-TITRATION OF RADIATION-BASED CONDITIONING

In other studies of mixed chimerism, lethal irradiation was utilized as a conditioning approach and reconstitution consisted of a mixture of T cell depleted (TCD) syngeneic plus TCD allogeneic bone marrow cells (Ildstad and Sachs, 1984, *Nature* 307: 168). In the present invention, a nonlethal radiation-based approach was used to achieve stable engraftment of allogeneic hematopoietic stem cells. In this model, the recipient was not fully cytoablated prior to allogeneic bone marrow transplantation, allowing the re-emergence of autologous stem cells within an environment of newly engrafted allogeneic bone marrow cells. Therefore, mixed allogeneic chimerism resulted even though only allogeneic bone marrow was infused as donor.

Titrations were performed to determine the minimum dose of TBI required to permit reliable engraftment of complete MHC-mismatched but minor antigen matched allogeneic bone marrow (B10.BR→B10). The dose of TBI administered directly correlated with the ability of allogeneic bone marrow cells to engraft (FIG. 1). Although allogeneic engraftment did not occur in all animals at doses of TBI below 6Gy, a significant increase in the number of animals which engrafted as allogeneic chimeras occurred at 6Gy. At this dose 50% of recipient animals that received 15×10$^6$ allogeneic bone marrow cells exhibited donor chimerism (FIG. 1). Allogeneic engraftment was reliably achieved in 100% of all animals conditioned with 7Gy. It is of note that most of the animals which engrafted exhibited a high level of allogeneic donor chimerism≥95% (Table 2). Evidently, in this model, allogeneic stem cells either engraft and result in nearly total allogeneic chimerism or they completely fail to engraft. The abrupt transition between failure of allogeneic engraftment to nearly complete allochimerism occurred near 6Gy, indicating that the "barrier(s)" to allogeneic chimerism is very specific, but once overcome, allogeneic engraftment occurs unimpeded.

TABLE 2

LEVEL OF DONOR CHIMERISM IN ANIMALS WITH ALLOGENEIC ENGRAFTMENT*

| Reconstitution | TBI Dose | Chimera # | % Donor Chimerism |
|---|---|---|---|
| 15 × 10$^6$ B10.Br→B10 | 5.5Gy | 1 | 99 |
| | 6Gy | 1 | 99 |
| | | 2 | 99 |
| | | 3 | 68 |
| | | 4 | 98 |
| | | 5 | 98 |
| | | 6 | 97 |
| | 7Gy | 1 | 97 |
| | | 2 | 99 |
| | | 3 | 99 |
| | | 4 | 100 |

*PBL typing was performed by flow cytometry 2 months post-reconstitution (B10.BR→B10) using anti-H2$^k$-FITC (B10.BR) and anti-H-2$^b$-FITC (B10) mAb. Animals are taken from those represented in FIG. 1. The percent donor chimerism (% B10.BR) is shown only for those animals which engrafted at each of the representative TBI doses. Results are pooled from 2 representative experiments out of a total of 5, and are normalized to 100%.

Similar studies were performed to examine whether engraftment of bone marrow from a donor strain (BALB/c; H-2$^d$) which was mismatched for MHC plus multiminor histocompatibility antigens could reliably occur at similar non-lethal doses of TBI. Resistance to alloengraftment was greater for BALB/c bone marrow than for MHC-disparate B10.BR bone marrow. Although comparable levels of engraftment with BALB/c and B10.BR allogeneic marrow occurred after lethal (9.5Gy) conditioning, less than 20% of recipients pretreated with 6Gy TBI prior to transplantation with BALB/c bone marrow cells [BALB/c→B10]exhibited any degree of allogeneic chimerism.

6.2.2. ENGRAFTMENT OF ALLOGENEIC BONE MARROW IS ENHANCED BY ANTI-LYMPHOCYTE GLOBULIN

Anti-lymphocyte globulin (ALG) is a polyclonal serum directed to multiple antigens expressed on lymphocytes which has often been used as an immunosuppressive agent (Monaco, 1991, Trans Proc 23(4): 2061). It produces a transient ablation of lymphocytes from blood and tissue. Early studies documented the induction of donor-specific tolerance in thymectomized mice given ALG plus donor bone marrow cells, leading to extensive study of its uses in transplantation (Wood et al., 1971, Trans Proc 3(1): 676). Donor cell engraftment in these studies was transient, if present at all. Although further attempts at generating permanent tolerance against fully allogeneic donor antigens with ALG alone have been less successful, survival of allografts has been prolonged in several species using ALG in combination with donor bone marrow cells or other immunosuppressive agents (Wood et al., 1971, Trans Proc 3(1): 676; Monaco, 1991, Trans Proc 23(4):2061). Therefore, it is possible that this serum preparation was able to deplete cells, although inefficiently, in the hematopoietic microenvironment to create space in a recipient.

To examine whether ALG would enhance the engraftment of allogeneic bone marrow in the established radiation-based model, recipient B10 mice received one of three conditioning approaches prior to transplantation with $40 \times 10^6$ or $15 \times 10^6$ BALB/c bone marrow cells: 70 mg/kg i.v. ALG given three days prior to bone marrow transplantation (Group 1); 5Gy of TBI on the day of transplantation (Group 2); or both ALG and TBI as administered in groups 1 and 2 (Group 3). The timing of ALG was chosen to assure maximum immunosuppression at the time of allogeneic bone marrow infusion (Wood et al., 1971, Trans Proc 3(1): 676). As in previous analysis, recipients were peripheral blood leukocyte (PBL)-typed for evidence of allogeneic engraftment 2 months following bone marrow transplantation. Allogeneic chimerism occurred in 85% of recipients conditioned with ALG and TBI (Group 3), while no evidence of alloengraftment was seen in animals receiving either ALG or TBI alone (Groups 1 and 2) (FIG. 2).

6.2.3. INFLUENCE OF CELL DOSE IN THE ALLOGENEIC INOCULUM ON ENGRAFTMENT WITH ALG AND TBI CONDITIONING

It has been demonstrated that a greater number of allogeneic donor cells are required to achieve reliable engraftment when compared with syngeneic reconstitution (Ildstad and Sachs, 1984, Nature 307: 168; Ildstad et al., 1986, J Exp Med 163: 1343). This has been termed alloresistance to engraftment. To examine the influence of donor cell number on the ability of ALG and TBI to enhance alloengraftment, dose-titration studies were performed in which the above established radiation plus ALG conditioning were utilized. Recipients were conditioned as above prior to receiving $40 \times 10^6$, $15 \times 10^6$, or $5 \times 10^6$ BALB/c bone marrow cells. The percentage of allogeneic donor-derived cells detected in the peripheral blood of the recipient (i.e. donor chimerism) increased in relation to the initial number of donor cells transplanted (Table 3). All animals appeared healthy and had no stigmata of GVHD although they had received untreated bone marrow cells.

TABLE 3

INFLUENCE OF CELL DOSE OF ALLOGENEIC BONE MARROW INOCULUM ON THE LEVEL OF DONOR CHIMERISM[a]

| GROUP | RECONSTITUTION | ANIMAL | % BALB/c PBL |
|---|---|---|---|
| 1 | $40 \times 10^6$ BALB/c→B10 | 1 | 87 |
|   |   | 2 | 86 |
|   |   | 3 | 87 |
|   | $15 \times 10^6$ BALB/c→B10 | 1 | 30 |
|   |   | 2 | 71 |
|   |   | 3 | 75 |
|   |   | 4 | 0 |
|   | $5 \times 10^6$ BALB/c→B10 | 1 | 1 |
|   |   | 2 | 0 |

[a]PBL typing was performed by flow cytometry 2 months post-reconstitution using anti-H-$2^d$-FITC and anti-H-$2^b$-FITC mAb. Results are from one of three representative experiments and are normalized to 100%.

6.2.4. ALLOGENEIC ENGRAFTMENT IS ENHANCED BY THE ADDITION OF CYCLOPHOSPHAMIDE TO THE ESTABLISHED RADIATION-BASED CONDITIONING

CyP is an alkylating agent used widely in treatment of lymphohematopoietic malignancies, such as leukemia (Gershwin et al., 1974, Annals Int Med 80: 531; Copelan and Deeg, 1992, Blood 80(7): 1648). It has been demonstrated to increase leukemic cell killing and reduce tumor relapse (Copelan and Deeg, 1992, Blood 80(7): 1648). CyP also exhibits immunosuppressive effects, by killing rapidly proliferating cells and resting lymphoid cells, with an impairment of both humoral and cellular responses (Mayumi et al., 1987, Transplantation 44(2): 286). Although conditioning with CyP alone does not result in allogeneic engraftment, combination therapies have proven useful in permitting engraftment of bone marrow from HLA-identical siblings (Graw et al., 1972, Transplantation 14: 79).

In order to assess the ability of CyP to enhance alloengraftment in the established radiation-based model, B10 mice were treated with one of three conditioning approaches prior to transplantation with $40 \times 10^6$ B10.BR or BALB/c bone marrow cells. Mice received 200 mg/kg i.p. of CyP alone (Group 1); 5Gy of TBI on the day of transplantation (Group 2); or 5 Gy TBI followed by CyP 2 days later (Group 3). Animals were PBL typed 2 months following reconstitution. Engraftment of allogeneic bone marrow occurred in nearly all recipients receiving 5Gy TBI plus CyP (FIG. 3). The degree of donor chimerism achieved was >90% in all chimeras conditioned with this approach. In contrast, all animals treated with TBI or CyP alone failed to engraft (Groups 1 and 2).

6.2.5. INFLUENCE OF TIMING OF TBI ON ALLOENGRAFTMENT IN RECIPIENTS CONDITIONED WITH ANTI-LYMPHOCYTE GLOBULIN OR CYCLOPHOSPHAMIDE

To examine the influence of timing of radiation on the engraftment of allogeneic bone marrow, recipient B10 mice were irradiated with 5Gy TBI one week prior to transplantation with $40 \times 10^6$ BALB/c allogeneic bone marrow cells. Additional animals, prepared in an identical fashion, received 70 mg/kg i.v. of ALG three days prior to transplantation or received 50 mg/kg i.p. CyP six, five, four, and three days prior to transplantation.

Animals conditioned with 5Gy of radiation alone failed to engraft even if the radiation was administered one week prior to transplantation (FIG. 4). Although 75% of the recipients exhibited allogeneic chimerism when treated with ALG plus TBI administered on the day of bone marrow transplantation, this enhancement of alloengraftment did not occur when TBI was given one week prior to transplantation. In contrast, the timing of TBI had little effect on the enhancement of alloengraftment seen with CyP. Nearly 75% of all recipient mice treated with TBI and CyP engrafted regardless of donor-strain or whether the CyP was administered before or shortly after the TBI (n=15) (FIG. 4). All of these chimeras exhibited ≧90% allogeneic donor chimerism.

All of the above approaches indicate that the hematopoietic microenvironment plays a major role in bone marrow engraftment.

6.2.6. CHARACTERIZATION OF A NONLETHAL RADIATION-BASED APPROACH FOR CYTOREDUCTION

To assure that the conditioning described herein was "nonlethal" with respect to overall morbidity and hematopoietic viability, control mice were conditioned but did not receive an allogeneic bone marrow transplant. Survival of the animals was excellent (FIG. 5), and none of the regimens used in this study resulted in any observable morbidity, i.e. diarrhea, cachexia, lassitude, hunched gate, dermatitis, alopecia, or anorexia. Moreover, these conditioning regimens were not lethal to the host hematopoietic stem cell since autologous repopulation resulted.

6.2.7. NONLETHAL MIXED CHIMERAS: EVIDENCE FOR MULTILINEAGE MIXED CHIMERISM

Mixed allogeneic chimeras conditioned with lethal TBI (9.5Gy) exhibit stable mixed chimerism of lymphoid and myeloid lineages, including T cells, B cells, NK cells, erythrocytes, platelets, and macrophages. To determine whether mixed allogeneic chimeras prepared with nonlethal conditioning exhibited selective syngeneic, allogeneic or mixed chimerism of individual hematolymphopoietic lineages, studies were undertaken to determine the proportion of cells within each lineage which were host (B10) or donor (BALB/c)-derived.

Animals which exhibited evidence for engraftment by PBL typing also had allogeneic cells of donor origin detected for each of the individual hematolymphopoietic lineages produced by the stem cell (FIG. 6A, 6B and 6C). The contribution of donor-derived cells varied among each of the lineages in the ten animals tested, with T lymphocytes ranging from 3.6 to 100%; B lymphocytes from 3.8 to 99%; NK cells from 9.8 to 96%; and macrophages from 21 to 76%. It was also influenced by the conditioning approach utilized.

6.2.8. EVIDENCE THAT ERYTHROCYTES AND PLATELETS IN ALLOGENEIC CHIMERAS ARE OF BOTH SYNGENEIC AND ALLOGENEIC ORIGIN

In order to analyze the proportion of donor and host erythrocytes (RBC) and platelets, allogeneic chimeras were prepared using BALB/c (H-$2^d$) and B10 (H-$2^b$) donor/recipient strain combinations which differ at the Glucose Phosphate Isomerase-1 (GPI-1) isoenzyme. All except one of the chimeras with known allogeneic PBL chimerism also exhibited RBC and platelets of allogeneic origin (Table 4). The proportion of allogeneic chimerism differed between each of the various lineages in individual animals, suggesting that the degree of allogeneic chimerism may be independently regulated for each hematopoietic lineage.

TABLE 4

PHENOTYPE OF PLATELETS AND ERYTHROCYTES IN MIXED ALLOGENEIC CHIMERAS[a]

| Reconstitution | TBI-based regimen | % BALB/c platelets | % BALB/c RBC | % BALB/c lymphoid cells |
|---|---|---|---|---|
| BALB/c→B10 | 5Gy + ALG | 55 | 64 | 86 |
|  |  | 0 | 0 | 30 |
|  |  | 14 | 30 | 71 |
|  | 5Gy + CyP | 71 | 100 | 99 |
|  |  | 78 | 100 | 98 |
|  |  | 69 | 100 | 91 |
|  |  | 31 | 100 | 92 |
| Normal B10 | — | 0 | 0 | 0 |
| Normal BALB/c | — | 100 | 100 | 99 |

[a]One representative experiment for phenotyping of platelets and erythrocytes by GPI-isomerase assay, and enzyme for which B10 and BALB/c mice differ. Lymphoid typing was performed by flow cytometry using anti-Class I H-$2^b$ and H-$2^d$ Mab. Analyses were performed using the forward and side scatter characteristic for the lymphoid gate. Results were normalized to 100% Animals were typed 2 months post reconstitution.

The single animal which exhibited lymphoid chimerism without evidence of allogeneic platelets or erythrocytes demonstrated stable lymphoid chimerism for ≧75 days post reconstitution. The lack of multilineage chimerism may be secondary to selective lineage regulation or may indicate engraftment of a lymphoid progenitor rather than engraftment of the pluripotent stem cell itself. All recipients which failed to exhibit PBL chimerism also had no evidence for allogeneic chimerism of erythroid or platelet lineages.

6.2.9. EVIDENCE FOR SPECIFIC TOLERANCE IN VIVO TO DONOR-TYPE SKIN GRAFTS

Mixed allogeneic chimeras prepared with nonlethal conditioning were tested for evidence of donor-specific tolerance in vivo by skin-grafting. B10 recipient mice received full thickness tail skin grafts of recipient, donor (B10.BR or BALB/c), or third-party origin (BALB/c, DBA, or B10.BR) 1 to 7 months following nonlethal conditioning and reconstitution (BALB/c→B10; B10.BR→B10). Grafts were read blindly and assessed on a daily basis for signs of rejection. In all recipients there was an absolute correlation between engraftment and tolerance, since mice with documented chimerism accepted donor-type skin grafts yet rejected MHC-disparate third-party skin grafts with a time course similar to identically-conditioned but unreconstituted controls (FIG. 7). All recipients which failed to exhibit allogeneic chimerism (<0.5%) promptly rejected both donor and third-party skin grafts.

6.2.10. FUNCTIONAL DONOR-SPECIFIC TOLERANCE IN VITRO

Nonlethally conditioned chimeras were assessed for donor-specific tolerance and immunocompetence in vitro using MLR and CML assays directed against donor and third-party antigens. Lymphocytes from chimeras which had evidence for allogeneic engraftment were functionally tolerant to both host (B10), and donor-strain (B10.BR or BALB/c) alloantigens but were reactive to third-party alloantigens in an MLR assay (BALB/c or BR10.BR, respectively) (Table 5). All similarly treated recipients without detectable allogeneic chimerism were reactive to both donor and third-party alloantigens.

Similarly, lymphocytes from recipient animals with allogeneic chimerism failed to lyse targets with host (B10) or donor (B10.BR) alloantigens, but were fully capable of third-party (BALB/c) target lysis in CML (FIG. 8A–8C). Lymphocytes from control animals without chimerism exhibited reactivity directed against all MHC-disparate targets.

were transferred. As the dosage of TBI increased, there was also a proportional increase of the percentage of donor cell engraftment in the recipients. FIG. 11 illustrates that when the conditioning was performed at 3Gy of TBI, the combined use of TBI, ALG and CyP was the only method capable of producing a substantial percentage of donor cell engraftment.

TABLE 5

REACTIVITY OF NONLETHALLY CONDITIONED MIXED ALLOGENEIC CHIMERAS IN ONE-WAY MLR[a]

| Animal | [³H]-Thymidine Incorporation (cpm ± SEM) | | | |
|---|---|---|---|---|
| | Anti-B10 | Anti-BR | Anti-BALB/c | Self anti-self |
| Normal B10 | 3057 ± 133 | 43,223 ± 3,838 | 58,135 ± 3,887 | — |
| Normal B10.BR | 40,900 ± 241 | 3,608 ± 446 | 59,537 ± 2,510 | — |
| Chimera 1 | 7,173 ± 883 | 3,507 ± 208 | 86,892 ± 3,763 | 2,001 ± 127 |
| Chimera 2 | 5,264 ± 886 | 4,077 ± 527 | 67,019 ± 777 | 3,175 ± 105 |

| Animal | Stimulation Index[b] | | |
|---|---|---|---|
| | B10 | B10.BR | BABL/c |
| Normal B10 | 1.0 | 14.1 | 19.0 |
| Normal B10.BR | 11.3 | 1.0 | 16.5 |
| Chimera 1 | 3.6 | 1.7 | 43.4 |
| Chimera 2 | 1.7 | 1.3 | 21.1 |

[a]Mean ± SEM of triplicate cultures in 1:1 responder-to-stimulator ratio. Animals were tested 2–6 months following reconstitution. This is one of five representative experiments. B10.BR bone marrow was infused into B10 recipients for each of the chimeras shown.
[b]Stimulation index is a ratio of the cpm generated in response to a given stimulator over the baseline cpm generated in response to the host. (Chimera anti-stimulator/Chimera anti-self)

6.2.11. NONLETHAL PREPARATIVE REGIMENS RESULT IN STABLE ALLOGENEIC CHIMERISM AND EXCELLENT LONG-TERM RECIPIENT SURVIVAL AND NO EVIDENCE FOR GVHD

All allogeneic chimeras which engrafted with allogeneic donor bone marrow (n=51) exhibited excellent survival and early evidence of donor chimerism by 3.5 to 4 weeks following bone marrow transplantation. Chimerism remained stable throughout a minimum follow-up of 3 to 4 months post reconstitution. None of the animals had evidence of GVHD for up to 8 months in follow-up. The overall mortality was less than 1%.

6.2.12. ALLOGENEIC ENGRAFTMENT AFTER CONDITIONING WITH NONLETHAL TOTAL BODY IRRADIATION, ANTI-LYMPHOCYTE GLOBULIN AND CYCLOPHOSPHAMIDE

The following study was carried out to examine whether the conditioning of a recipient with the combined treatment of ALG and CyP would reduce the dosage of TBI necessary to result in stable engraftment of allogeneic donor cells. B10 mice were treated with ALG at 2 mg/mouse i.v. at day −3 before bone marrow transplantation. Then on day 0, the same animals were treated with various doses of TBI and 15×10⁶ B10.BR or BALB/c bone marrow cells, followed by CyP (200 mg/kg) injection two days later. Mixed allogeneic chimerism was achieved in ≧90% of the animals conditioned with 3Gy TBI, ALG and CyP. At 2 Gy TBI, a lower but significant percentage of recipients were also engrafted with donor cells (FIG. 9). FIG. 10 shows that even at 2 Gy, the combined treatment of these regimens allowed a definite percentage of donor cell engraftment. This TBI dosage could even be reduced to 1Gy if higher numbers of donor cells Although 200 mg/kg of CyP was used as the dose of choice, it was shown that the entire range of 50–200 mg/kg of CyP was able to condition a recipient in combination with TBI and ALG. Similarly, ALG yielded positive conditioning results when administered at 0.5–2 mg/animal. Additionally, a higher number of donor cells always produced higher levels of engraftment. This was demonstrated when BALB/c donor cells were used in place of B10.BR. Since BALB/c cells were incompatible with B10 recipients at both the MHC and minor antigens, it generally required a stronger conditioning treatment to achieve BALB/c cell engraftment than that necessary for B10.BR. This could be accomplished by increasing the dosage of any one of the three regimens, or alternatively, by a higher number of donor cells.

The engraftment of donor cells was stable and in diverse blood cell lineages, including T cells, B cells, NK cells, RBC, granulocytes, platelets and macrophages. When the animals were transplanted with skin grafts from the donor, donor-specific transplantation tolerance was observed, but third party grafts were rejected. Similar pattern of reactivity was confirmed in MLR and CML. The combined use of three regimens was non-lethal, since all treated animals survived for more than 100 days, while all mice treated with TBI at 9.5Gy died by day 10.

7. EXAMPLE: XENOGENEIC BONE MARROW CELLS ENGRAFT IN RECIPIENTS CONDITIONED BY NON-LETHAL METHODS

7.1. RESULTS

A similar non-lethal radiation-based model has been established in which rat bone marrow stem cells engrafted stably (≧8 months) in mouse recipients. A sigmoidal curve was also observed when the percentage of animals with donor cell engraftment was compared with varying doses of irradiation (FIG. 1). This curve was shifted slightly to greater radiation doses as compared to the conditions sufficient for allogeneic engraftment, since only 28.6% of the animals engrafted at 6.5 Gy. A higher proportion of rat donor cell engraftment occurred with increasing sub-lethal doses of radiation. At 7.5 Gy, all mice demonstrated evidence of rat stem cell engraftment. Again, the animals exhibited multilineage chimerism, including the presence of rat $\alpha\beta$-TCR$^+$T cells, B cells, NK cells, monocytes, platelets and red blood cells.

In addition, the xenogeneic chimeras also displayed functional donor-specific tolerance to both host and donor cells, while their responses to MHC-disparate third-party rat or mouse stimulator cells remained intact. In vivo, the chimeras accepted xenogeneic pancreatic islet grafts from the same donors, whereas they readily rejected third-party rat islets. Thus, the data obtained from xenogeneic bone marrow transplantation studies confirmed the successful use of a non-lethal conditioning regimen, indicating the importance of the hematopoietic microenvrionment in xenogeneic donor cell engraftment.

8. EXAMPLE: ALLOGENEIC AND XENOGENEIC ENGRAFTMENT AFTER CONDITIONING WITH TOTAL LYMPHOID IRRADIATION

In addition to TBI, TLI was also tested in conditioning recipients for bone marrow transplantation. As a single dose, TLI was simply a modified form of TBI in that the method of delivery was the same way, except that only certain parts of the recipient's body was exposed to the irradiation. Since TLI was a less aggressive and ablative approach, its dosage could be increased up to 10 Gy without lethal consequences. In the following study, baboons were treated with a single dose of 7.5 Gy of TLI at day 0 followed by transfer of allogeneic baboon bone marrow cells with at least one MHC disparity. In addition, certain animals were further treated with a single dose of CyP (50 mg/kg) at day +2, or two doses of CyP at day −3 and −2. The results demonstrate that the majority of baboons conditioned with 7.5Gy TLI and two doses of CyP produced stable ($\geq$36 weeks) engraftment of up 30% donor cells. TLI with a single dose of CyP produced stable donor cell engraftment in about 50% of the treated animals. Several of the engrafted animals exhibited donor-specific tolerance in MLR assays after three months. TLI alone gave rise to donor cell engraftment in about 25% of the recipients. However, the engraftment occurred at very low levels, which was detectable only by molecular typing techniques.

Xenogeneic transplantation with human cells was also performed in baboons conditioned with TLI. Since xenogeneic barriers were usually more difficult to overcome, a baboon was treated with CyP at day −3, −2 and −1, and 9.5 Gy TLI on day 0, followed by 22×10$^8$/kg human vertebral body bone marrow cells that had been antibody-depleted to remove GVHD-producing cells such as T cells, B cells and NK cells. The animal produced chimerism with 15% human cells two months after transplantation, with no GVHD or significant morbidity.

The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for conditioning a recipient for bone marrow transplantation comprising subjecting the recipient to treatment with a non-lethal dose of total body irradiation, an alkylating agent and an antibody or an active fragment thereof, followed by transplantation with a donor cell preparation containing hematopoietic stem cells which are not compatible with the recipient at the major histocompatibility complex, to achieve stable engraftment of donor hematopoietic stem cells.

2. The method of claim 1 in which the dose is between 1 Gy and 7 Gy.

3. The method of claim 1 in which the alkylating agent is cyclophosphamide.

4. The method of claim 1 in which the antibody is anti-lymphocyte globulin.

5. The method of claim 1 in which the antibody is of monoclonal origin.

6. The method of claim 5 in which the antibody is conjugated to an anti-proliferative agent.

7. The method of claim 6 in which the anti-proliferative agent is a chemotherapeutic drug.

8. The method of claim 6 in which the anti-proliferative agent is a radioactive isotope.

9. The method of claim 6 in which the anti-proliferative agent is a toxin.

10. The method of claim 1 in which the antibody is reactive with a bone marrow stromal cell.

* * * * *